(12) United States Patent
Harris et al.

(10) Patent No.: US 7,437,197 B2
(45) Date of Patent: Oct. 14, 2008

(54) MEDICAL LEAD AND MANUFACTURING METHOD THEREFOR

(75) Inventors: Charmaine K. Harris, Woodbury, MN (US); Scott J. Robinson, Forest Lake, MN (US); Jamie A. Mattson, Brooklyn Park, MN (US); Thomas E. Cross, Jr., St. Francis, MN (US)

(73) Assignee: Medtronic, Inc., Minneapolis, MN (US)

( * ) Notice: Subject to any disclaimer, the term of this patent is extended or adjusted under 35 U.S.C. 154(b) by 627 days.

(21) Appl. No.: 10/835,937

(22) Filed: Apr. 30, 2004

(65) Prior Publication Data

US 2005/0090885 A1   Apr. 28, 2005

Related U.S. Application Data

(60) Provisional application No. 60/513,710, filed on Oct. 23, 2003.

(51) Int. Cl.
  *A61N 1/05* (2006.01)
(52) U.S. Cl. .................................. 607/115; 607/116
(58) Field of Classification Search ......... 607/115–117, 607/119, 122–123; 600/372, 373
See application file for complete search history.

(56) References Cited

U.S. PATENT DOCUMENTS

| | | | |
|---|---|---|---|
| 3,646,940 A | 3/1972 | Timm et al. | |
| 3,724,467 A | 4/1973 | Avery et al. | |
| 4,141,365 A | 2/1979 | Fischell et al. | |
| 4,285,347 A | 8/1981 | Hess | |
| 4,379,462 A | 4/1983 | Borkan et al. | |
| 4,573,481 A | 3/1986 | Bullara | |
| 4,722,761 A * | 2/1988 | Cartmell et al. | 156/242 |
| 4,735,208 A | 4/1988 | Wyler et al. | |
| 4,800,898 A | 1/1989 | Hess et al. | |
| 4,920,979 A | 5/1990 | Bullara | |
| 5,121,754 A | 6/1992 | Mullett | |
| 5,249,574 A | 10/1993 | Bush et al. | |
| 5,255,691 A | 10/1993 | Otten | |
| 5,391,200 A | 2/1995 | KenKnight et al. | |
| 5,397,342 A | 3/1995 | Heil, Jr. et al. | |
| 5,417,719 A | 5/1995 | Hull et al. | |
| 5,505,201 A | 4/1996 | Grill, Jr. et al. | |
| 5,643,330 A | 7/1997 | Holsheimer et al. | |

(Continued)

FOREIGN PATENT DOCUMENTS

EP   1048270   11/2000

(Continued)

*Primary Examiner*—Carl H. Layno
*Assistant Examiner*—Brian T Gedeon

(57) ABSTRACT

A method of manufacturing a medical lead comprising a lead body with at least one conductor and an elongate paddle having an electrode array. A first section is formed having a first butt bond by butt bonding an end of a first substantially flat and elongate member to an end a second substantially flat and elongate member. A second section is formed having a second butt bond by butt bonding an end of a third substantially flat and elongate member to an end a fourth substantially flat and elongate member. The first section is laminated to the second section to form the elongate paddle of the medical lead with the first butt bond longitudinally offset from the second butt bond. A medical lead made by exemplary embodiments of the method is also described.

27 Claims, 27 Drawing Sheets

U.S. PATENT DOCUMENTS

| | | | |
|---|---|---|---|
| 5,669,882 A | 9/1997 | Pyles | |
| 5,689,877 A | 11/1997 | Grill, Jr. et al. | |
| 5,702,429 A | 12/1997 | King | |
| 5,730,754 A | 3/1998 | Obenchain | |
| 5,902,236 A | 5/1999 | Iversen | |
| 5,913,882 A | 6/1999 | King | |
| 5,964,702 A | 10/1999 | Grill, Jr. et al. | |
| 6,010,493 A | 1/2000 | Snoke | |
| 6,024,702 A | 2/2000 | Iversen | |
| 6,052,608 A | 4/2000 | Young et al. | |
| 6,055,456 A | 4/2000 | Gerber | |
| 6,066,165 A | 5/2000 | Racz | |
| 6,104,960 A | 8/2000 | Duysens et al. | |
| 6,161,047 A | 12/2000 | King et al. | |
| 6,185,463 B1 | 2/2001 | Baudino | |
| 6,205,361 B1 | 3/2001 | Kuzma et al. | |
| 6,233,488 B1 | 5/2001 | Hess | |
| 6,236,892 B1 | 5/2001 | Feler | |
| 6,249,707 B1 | 6/2001 | Kohnen et al. | |
| 6,277,094 B1 | 8/2001 | Schendel | |
| 6,292,702 B1 | 9/2001 | King et al. | |
| 6,308,103 B1 | 10/2001 | Gielen | |
| 6,309,401 B1 | 10/2001 | Redko et al. | |
| 6,360,750 B1 | 3/2002 | Gerber et al. | |
| 6,385,491 B1 | 5/2002 | Lindemans et al. | |
| 6,415,187 B1 | 7/2002 | Kuzma et al. | |
| 6,463,335 B1 | 10/2002 | Münch et al. | |
| 6,522,932 B1 | 2/2003 | Kuzma et al. | |
| 6,553,264 B2 | 4/2003 | Redko et al. | |
| 6,587,733 B1 | 7/2003 | Cross, Jr. et al. | |
| 6,697,677 B2 | 2/2004 | Dahl et al. | |
| 7,072,719 B2 * | 7/2006 | Vinup et al. | 607/117 |
| 2001/0025192 A1 | 9/2001 | Gerber et al. | |
| 2002/0022873 A1 | 2/2002 | Erickson et al. | |
| 2002/0035377 A1 | 3/2002 | Bardy et al. | |
| 2002/0035378 A1 | 3/2002 | Bardy et al. | |
| 2002/0035379 A1 | 3/2002 | Bardy et al. | |
| 2002/0035381 A1 | 3/2002 | Bardy et al. | |
| 2002/0035388 A1 | 3/2002 | Lindemans et al. | |
| 2002/0042642 A1 | 4/2002 | Gerber | |
| 2002/0052636 A1 | 5/2002 | Bardy et al. | |
| 2002/0107549 A1 | 8/2002 | Bardy et al. | |
| 2002/0111661 A1 | 8/2002 | Cross et al. | |
| 2002/0128700 A1 | 9/2002 | Cross | |
| 2002/0188339 A1 * | 12/2002 | Bischoff et al. | 607/122 |
| 2003/0028147 A1 | 2/2003 | Aves et al. | |
| 2003/0036787 A1 | 2/2003 | Redko et al. | |
| 2003/0055476 A1 | 3/2003 | Vinup et al. | |
| 2003/0069623 A1 | 4/2003 | Stypulkowski | |
| 2003/0135253 A1 | 7/2003 | Kokones et al. | |
| 2003/0204228 A1 | 10/2003 | Cross et al. | |
| 2004/0260310 A1 | 12/2004 | Harris | |
| 2005/0004638 A1 * | 1/2005 | Cross, Jr. | 607/117 |

FOREIGN PATENT DOCUMENTS

| | | |
|---|---|---|
| EP | 1048271 | 11/2000 |
| EP | 1048317 | 11/2000 |
| EP | 1048321 | 11/2000 |
| WO | WO99/49933 | 10/1999 |
| WO | WO99/55411 | 11/1999 |
| WO | WO99/56817 | 11/1999 |
| WO | WO99/56818 | 11/1999 |
| WO | WO01/00274 | 1/2001 |
| WO | WO01/24872 | 4/2001 |
| WO | WO01/58519 | 8/2001 |
| WO | 1181947 | 2/2002 |
| WO | WO02/13903 | 2/2002 |
| WO | WO02/072192 | 9/2002 |
| WO | WO03/011361 | 2/2003 |
| WO | WO03/013650 | 2/2003 |
| WO | WO03/018110 | 3/2003 |
| WO | WO03/018111 | 3/2003 |
| WO | WO03/018112 | 3/2003 |
| WO | WO03/018127 | 3/2003 |
| WO | WO03/018130 | 3/2003 |
| WO | WO03/039656 | 5/2003 |
| WO | WO03/059440 | 7/2003 |
| WO | WO03/090851 | 11/2003 |

* cited by examiner

MEDICAL LEAD AND MANUFACTURING METHOD THEREFOR

RELATED APPLICATION

This application claims priority to provisional U.S. Application Ser. No. 60/513,710, filed Oct. 23, 2003, which is hereby incorporated herein by reference.

FIELD OF THE INVENTION

This application relates generally to medical leads for electrical stimulation or sensing, methods of use or manufacture thereof, and more particularly to a paddle-style lead, for example, for spinal cord stimulation and methods of use and manufacture thereof.

BACKGROUND OF THE INVENTION

Paddles for paddle-type medical leads have been made by injection molding silicone material. Electrodes and conductors are placed in a mold before injection molding the silicone material. While such methods may work well to manufacture paddles of silicone material, they are believed to be less advantageous for manufacture of paddles formed of various polymeric materials, such as polyurethane.

SUMMARY OF EXEMPLARY EMBODIMENTS OF THE INVENTION

A medical lead is provided for electrical stimulation or sensing. Exemplary embodiments of the medical lead are adapted to facilitate repositioning, withdrawal or explanting the medical lead, as well as using the features of a flat lead paddle to anchor the lead to the connective tissue. Exemplary embodiments of the medical lead are adapted for percutaneous introduction of the medical lead through an introducer needle, such as a flattened Tuohy needle.

An exemplary embodiment of a method of manufacturing a medical lead generally comprises: (a) forming at least first, second, third and fourth substantially flat and elongate members, each member having first and second ends; (b) butt bonding the first end of the first member to the second end of the second member to form a first section with the junction of the first end of the first member and the second end of the second member constituting a first butt bond, the first section having first and second major surfaces; (c) butt bonding the first end of the third member to the second end of the fourth member to form a second section with the junction of the first end of the third member and the second end of the fourth member constituting a second butt bond, the second section having first and second major surfaces; (d) placing at least one electrode in the first section exposed through the first major surface of the first member, and placing at least one conductor in electrical communication with the electrode along the second major surface of the first member; and (e) attaching the first major surface of the second section to the second major surface of the first section to form the elongate paddle of the medical lead with the first butt bond longitudinally offset from the second butt bond.

In a second exemplary embodiment of a method of manufacturing a medical lead, the method generally comprises (a) forming a first section having a first butt bond by butt bonding an end of a first substantially flat and elongate member to an end a second substantially flat and elongate member; (b) forming a second section having a second butt bond by butt bonding an end of a third substantially flat and elongate member to an end a fourth substantially flat and elongate member; and (c) laminating the first section to the second section to form the elongate paddle of the medical lead with the first butt bond longitudinally offset from the second butt bond.

In a third exemplary embodiment of a method of manufacturing a medical lead, the method generally comprises (a) forming at least first, second, third and fourth substantially flat and elongate members, with each member having first and second ends; (b) butt bonding the first end of the first member to the second end of the second member to form a first section with the junction of the first end of the first member and the second end of the second member constituting a first butt bond, the first section having first and second major surfaces; (c) placing at least one electrode in the first section exposed through the first major surface of the first member, and placing at least one conductor in electrical communication with the electrode along the second major surface of the first member; (d) attaching the third member to a first portion of the second major surface of the first section with the first end of the third member longitudinally offset from the first butt bond and leaving a second portion of the second major surface of the first section exposed; and (e) attaching the fourth member to the second portion of the second major surface of the first section and butt bonding the second end of the fourth member to the first end of the third member with the butt bond of the first end of the third member and the second end of the fourth member constituting a second butt bond. This exemplary embodiment of the method thus forms an elongate paddle of the medical lead with the first butt bond longitudinally offset from the second butt bond.

In yet an exemplary embodiment of a medical lead, the medical lead generally comprises a generally flat paddle on the distal end of the lead body. The paddle has an electrode array comprising at least one electrode in electrical communication with the electrical conductor. The paddle is formed by a method comprising: (a) forming a first section having a first butt bond by butt bonding an end of a first substantially flat and elongate member to an end a second substantially flat and elongate member; (b) forming a second section having a second butt bond by butt bonding an end of a third substantially flat and elongate member to an end a fourth substantially flat and elongate member; and (c) laminating the first section to the second section to form the elongate paddle of the medical lead with the first butt bond longitudinally offset from the second butt bond.

An additional exemplary embodiment includes a medical lead having an identification marker for determining orientation or identifying the lead. For example, the marker may provide a definite indication of the direction of the lead (which way it is facing), and/or be coded to identify the model or serial number of a lead.

Yet another exemplary embodiment is a combination or set comprising a medical lead and a flattened needle. Preferably the combination further includes a plastic or elastomeric stylet that is cable of being withdrawn from the needle even if the needle has been subjected to plastic deformation.

Still another exemplary embodiment is a system comprising a medical lead and an implantable pulse generator. The system preferably includes at least one or two external programmer(s), such a physician programmer and a patient programmer.

These and other features are described hereinafter or in the drawings.

DETAILED DESCRIPTION OF EXEMPLARY EMBODIMENTS

Figure 1:
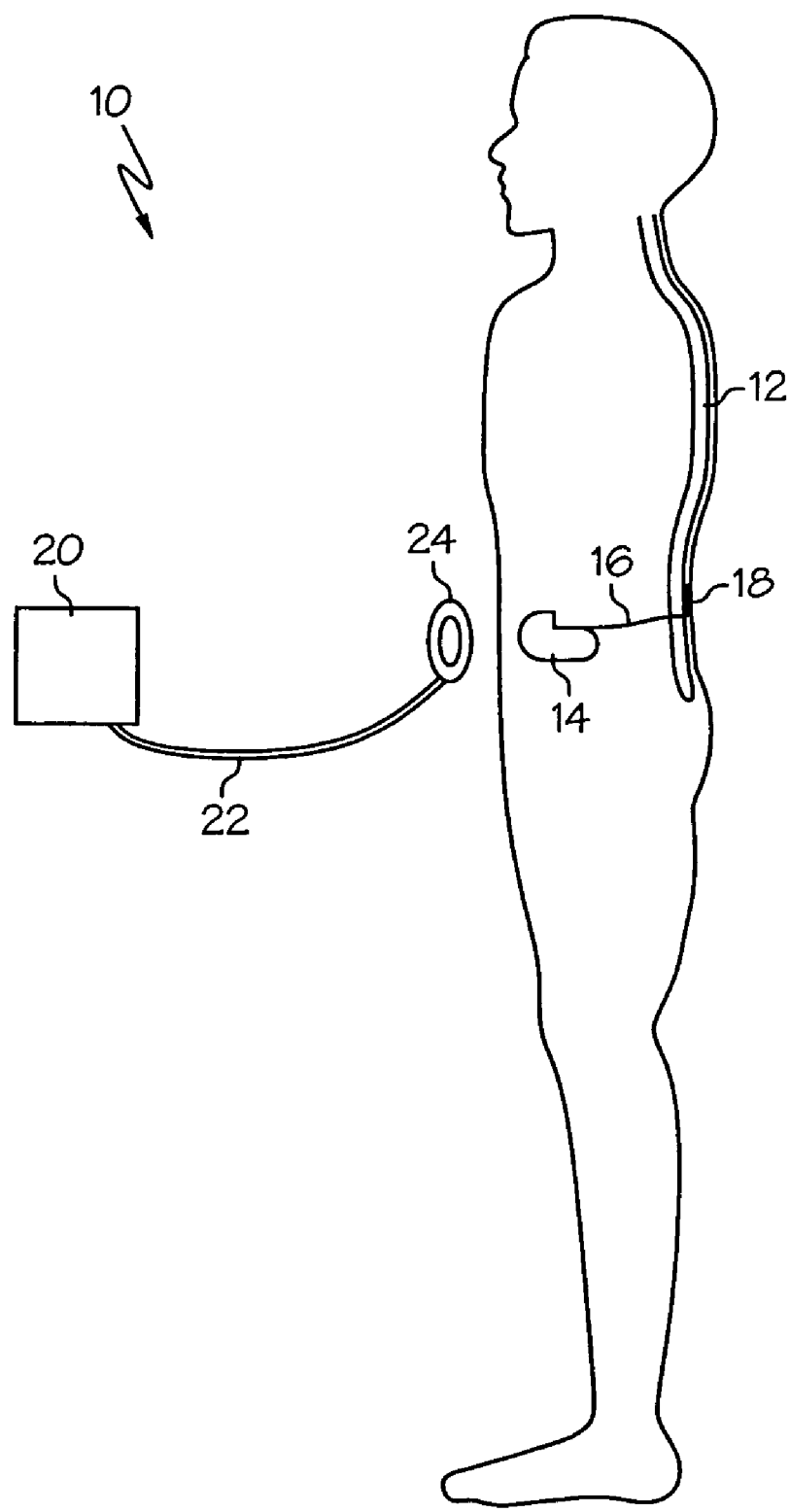
FIG. 1 is a schematic view of an exemplary embodiment of a system including a medical lead, implantable pulse generator (IPG) and programmer.

FIG. 1 is a schematic view of a patient 10 having an implant of a neurological stimulation system employing the present invention to stimulate spinal cord 12 of the patient. The preferred system employs implantable pulse generator (IPG) 14 to produce a number of independent stimulation pulses which are sent to spinal cord 12 by insulated lead 16 and coupled to the spinal cord by electrodes located at point 18. An extension, which includes a conductor, may also be used to electrically connect the IPG to the lead 16.

Implantable pulse generator 14 may be, for example, a neurostimulator, such as the neurostimulators available under the trade designations "Model 7425 Itrel™ 3 Neurostimulator" or "Model 7427 Synergy™ Neurostimulator," both available from Medtronic, Inc., Minneapolis, Minn. Exemplary embodiments of such implantable pulse generators 14 typically include a battery or other power source, a processor, and a connector header for connection of a lead or lead extension to the IPG, as well as a telemetry antenna to allow communication with the IPG to or from an external device.

This exemplary system may employ a programmer 20, which is coupled via conductor 22 to radio frequency antenna 24. This permits attending medical personnel to select the various pulse output options after implant using radio frequency communications. While the exemplary system employs fully implanted elements, systems employing partially implanted generators and radio-frequency coupling may also practice the present invention. The system may also include a patient programmer (similar at the schematic level to the programmer 20) allowing the patient to select or modify the stimulation therapy program.

While the preferred exemplary system employs fully implanted elements, systems employing partially implanted generators and radio-frequency coupling may also be used (e.g., similar to products sold by Medtronic, Inc. under the trademarks X-trel and Matrix).

Figure 2:
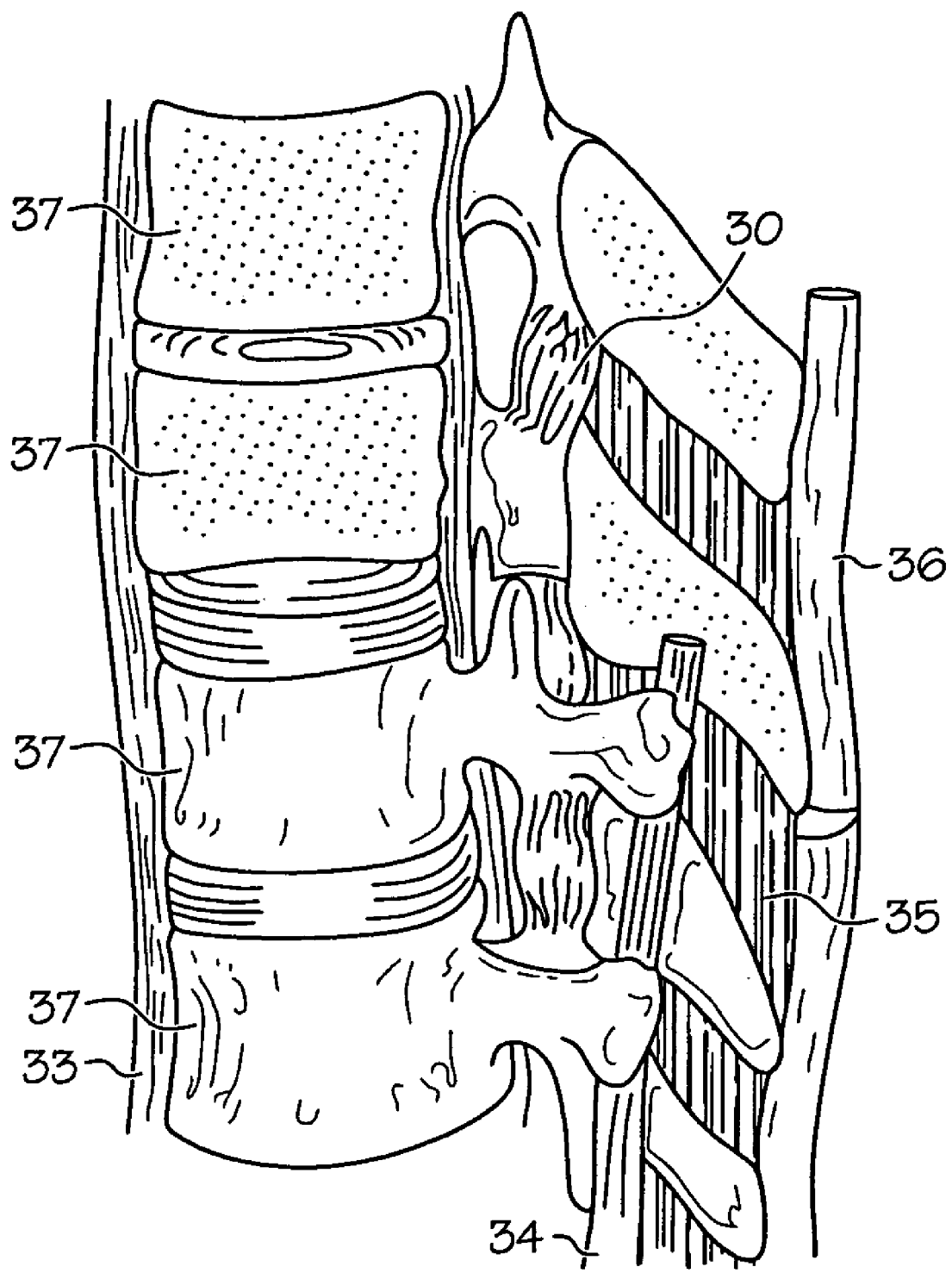
FIG. 2 illustrates various anatomical features of a portion of the vertebral column, including connective tissue, such as the ligamentum flavum through which medical leads are passed into the epidural space for electrical stimulation or sensing of the nerves of the spinal cord.
Figure 3:
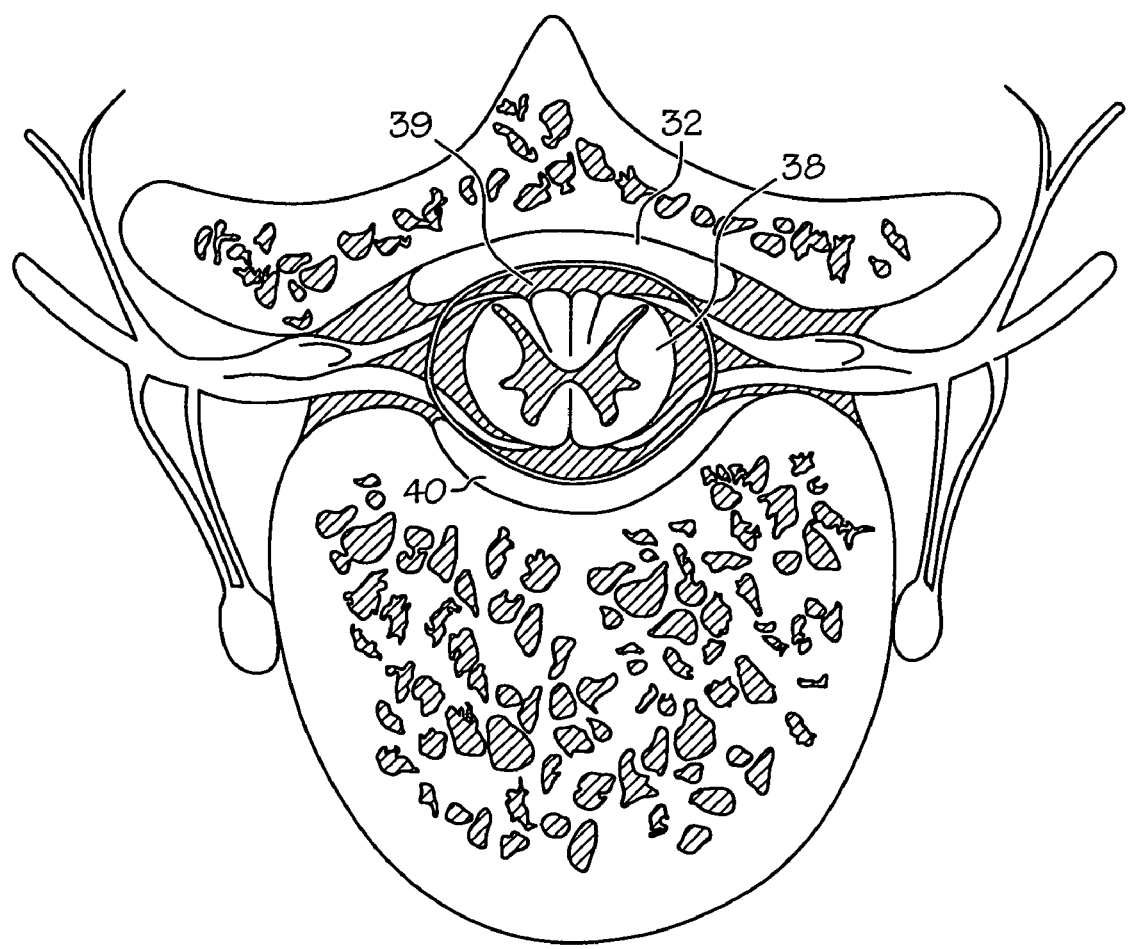
FIG. 3 is a cross sectional view along a transverse plane of a vertrebral column.
Figure 4:
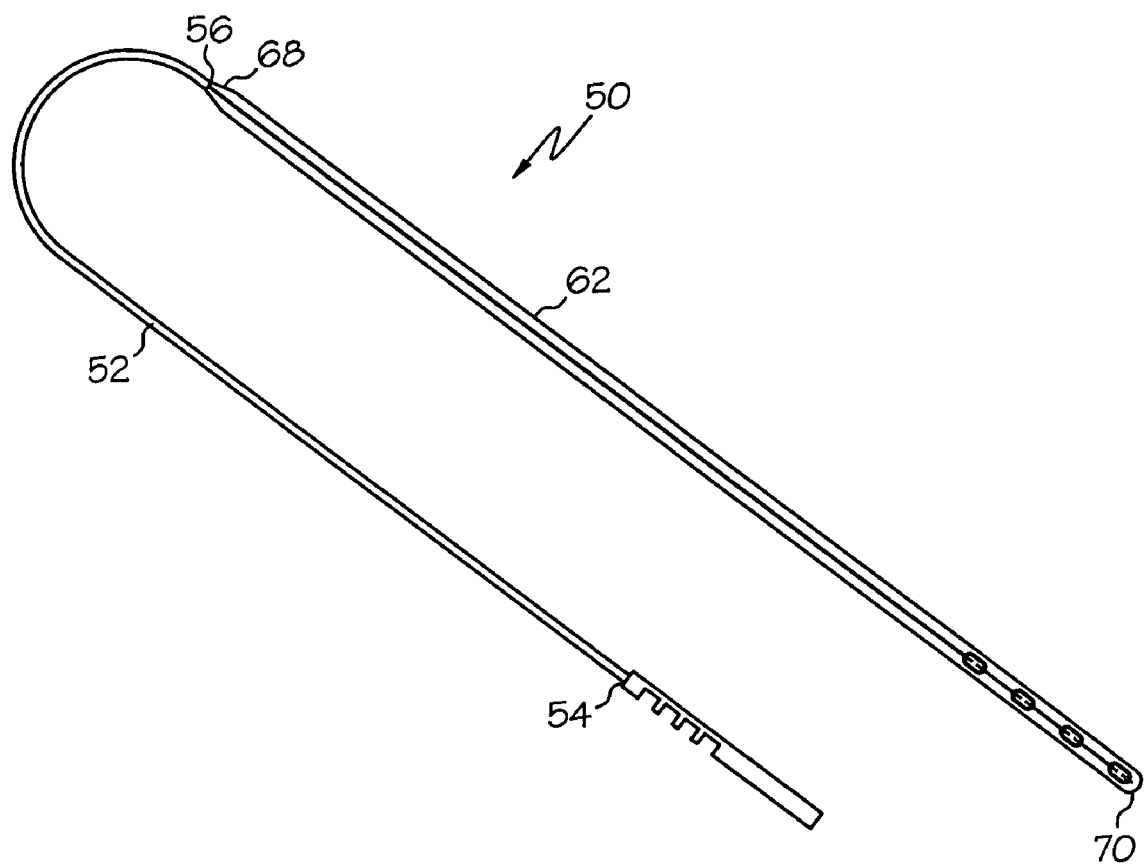
FIG. 4 is a plan view of an exemplary paddle-style medical lead of the invention.
Figure 5:
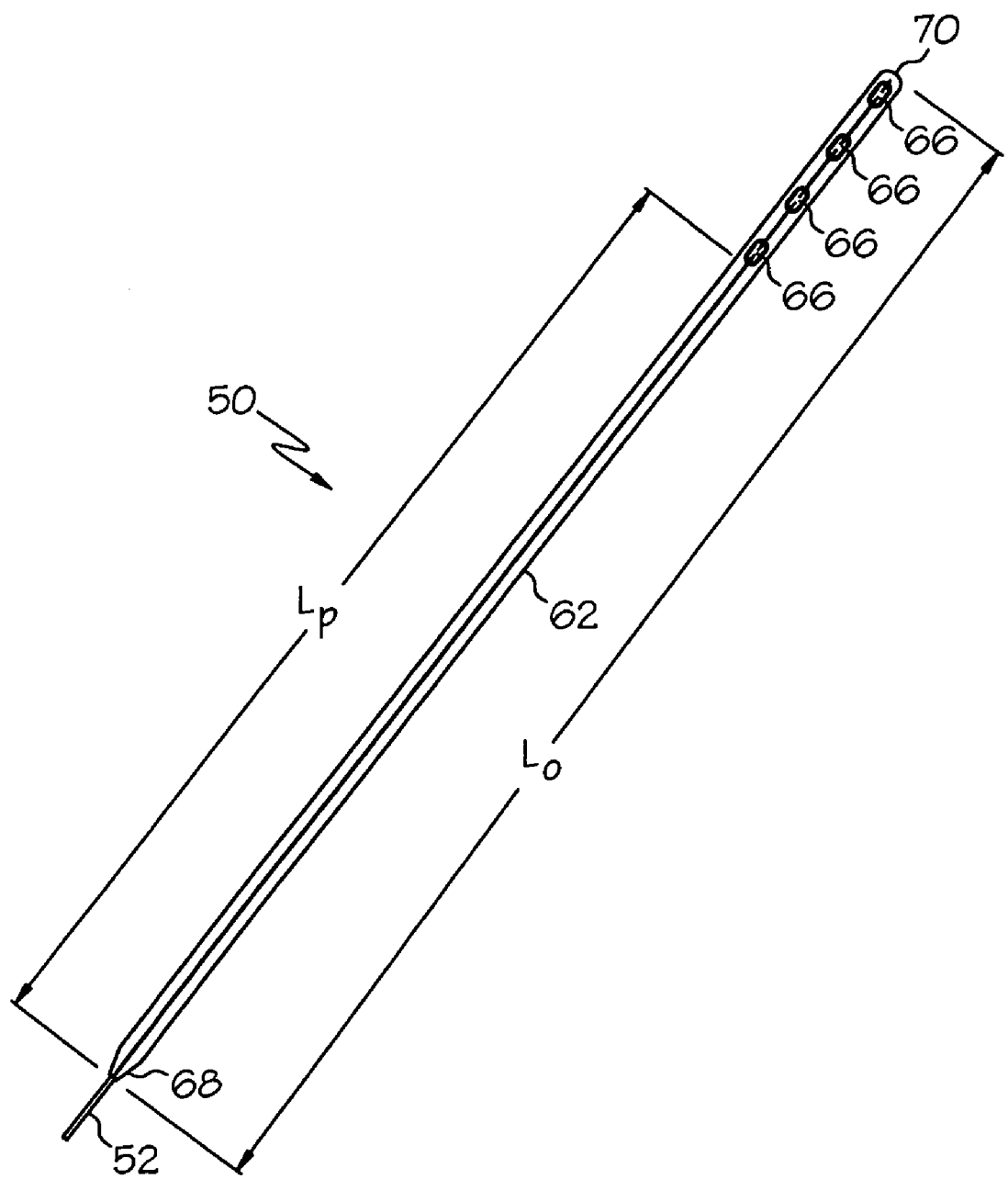
FIG. 5 is a plan view the paddle of FIG. 4.
Figure 6:
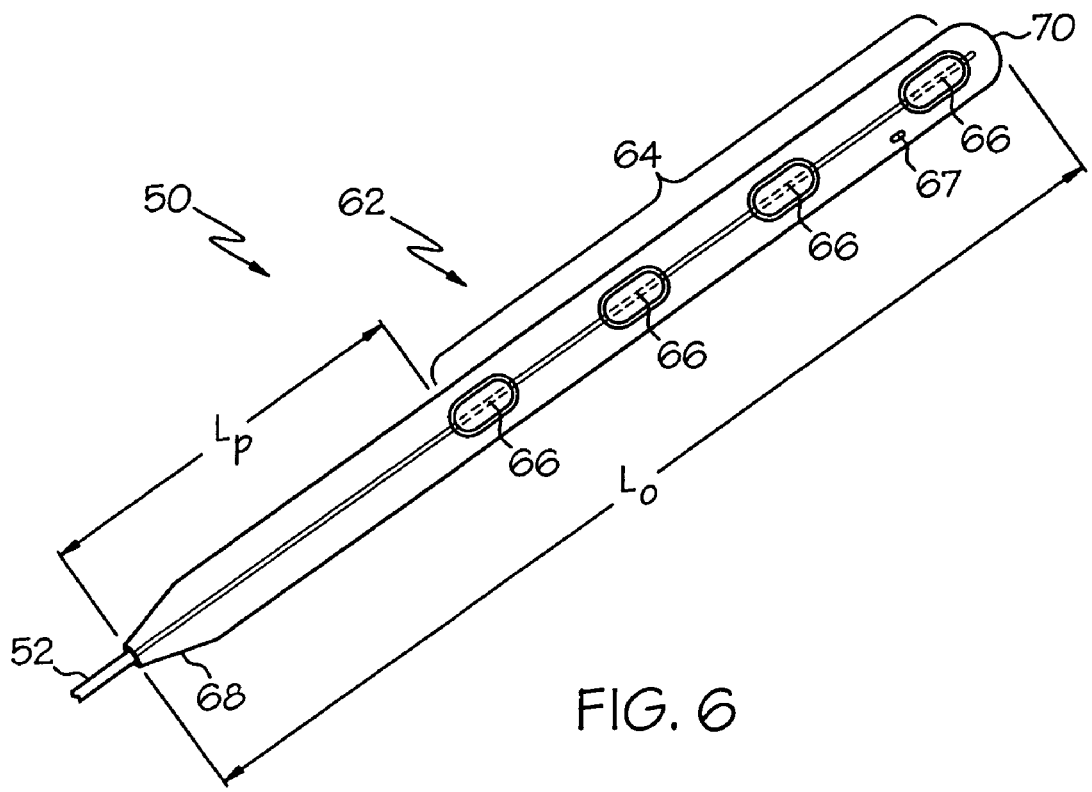
FIG. 6 is a partial view of a second exemplary embodiment of the paddle-style lead, illustrating among other things an orientation marker.

FIGS. 2 and 3 illustrate details of spinal or vertebral anatomy, including connective tissue, such as the ligamentum flavum 30 (FIG. 2) and the posterior epidural space 32 (FIG. 3). Exemplary embodiments of the medical lead 50 are adapted to be implanted through the ligamentum flavum 30 into the epidural space 32 into position for electrical spinal cord stimulation. FIG. 2 also illustrates, among other things, the anterior longitudinal ligament 33, intertransverse ligament 34, interspinal ligament 35, and supraspinal ligament 36, and, of course, vertebra 37. FIG. 3 also illustrates, among other things, the spinal cord 38, intrethecal space 39, and anterior epidural space 40.

FIGS. 4-8 show two exemplary embodiments of the paddle-style lead 50. The medical lead 50 comprises a generally round or tubular lead body 52 having proximal and distal ends 54 and 56, and at least one electrical conductor 58 (e.g., 4 or 8) extending between the proximal and distal ends. A connector or contact ring 60 is provided on the proximal end 54 of the lead body 52 in electrical communication with the electrical conductor 58. A generally flat paddle 62 is provided on the distal end 56 of the lead body 52.

An electrode array 64 is provided on the flat paddle 62 comprising at least one electrode 66 (e.g., four or eight electrodes) in electrical communication with the electrical conductor 58 (e.g., four or eight conductors corresponding to the number of electrodes). The paddle 62 has proximal and distal ends 68 and 70 and a length "$L_O$" extending between the proximal and distal ends. The electrode array 64 is displaced along the length of the paddle toward the distal end 70. For example, the portion of the flat paddle proximal of the electrode array has a length $L_P$ of at least 4 inches (100 mm), 3 inches (75 mm), 2 inches (50 mm) or 1-½ inches (40 mm).

In one preferred exemplary embodiment, four conductors are provided with each comprising fluoropolymer insulated 0.005 diameter MP35N—Ag core cables. Four connectors or contact rings 58 may be configured to constitute, for example, an in-line cylindrical connector system for connection to a lead extension or IPG. Four electrodes may also be provided each comprising platinum/iridium. Such exemplary embodiments may have a total lead length of 25 cm to 100 cm, e.g., 30, 45 and 60 cm standardized lengths. Of course, other dimensions, materials and number of electrodes could be employed, and these are provided for purposes of illustration only.

One exemplary paddle 62 may have a nominal length of 8 inches (20 cm), nominal width of 0.15 inches (3.8 mm), and a nominal thickness of 0.04 inches (1 mm). The paddle 62 may be formed, for example, of material including polyurethane, and in one exemplary embodiment is formed of generally transparent polyurethane material.

Figure 10:
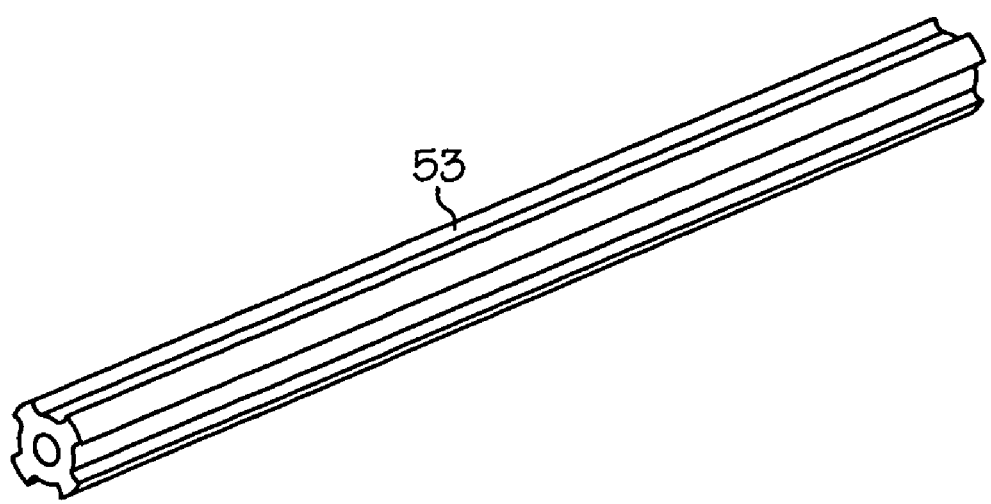
FIG. 10 is a perspective view of an exemplary center strut, which is one of two alternative preferred exemplary structures for use in the lead body of the medical lead of FIGS. 6-9.
Figure 11:
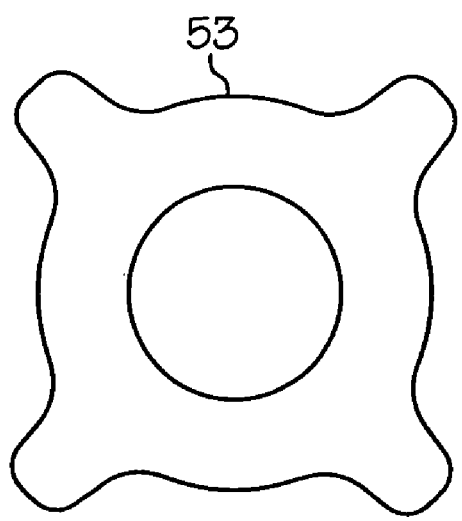
FIG. 11 is a cross sectional view of the exemplary center strut of FIG. 10, illustrating aspects of a center strut.
Figure 12:
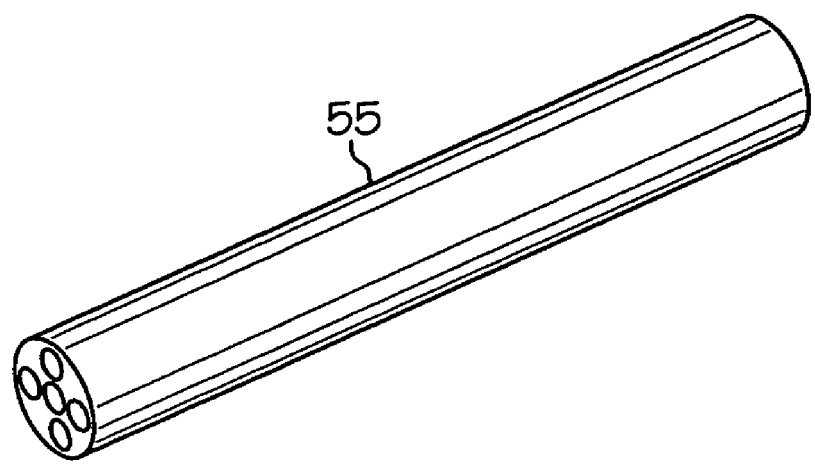
FIG. 12 is a perspective view of an exemplary pentalumen tubing, which is the other of two alternative preferred exemplary structures for use in the lead body of the medical lead of FIGS. 6-9.
Figure 13:
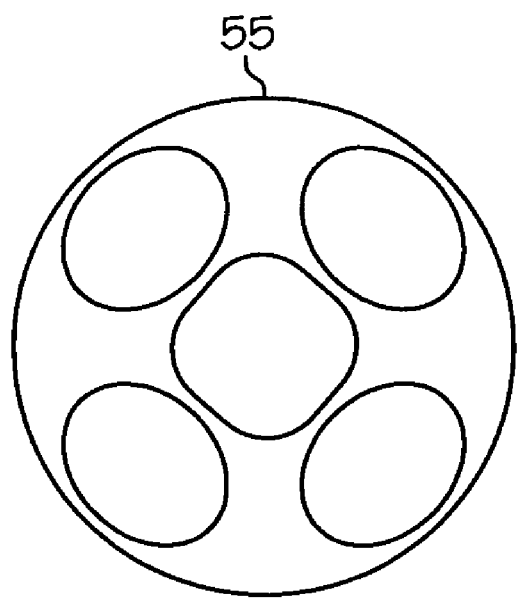
FIG. 13 is a cross sectional view of the exemplary pentalumen tubing of FIG. 12, illustrating illustrating aspects of pentalumen tubing.
Figure 14:
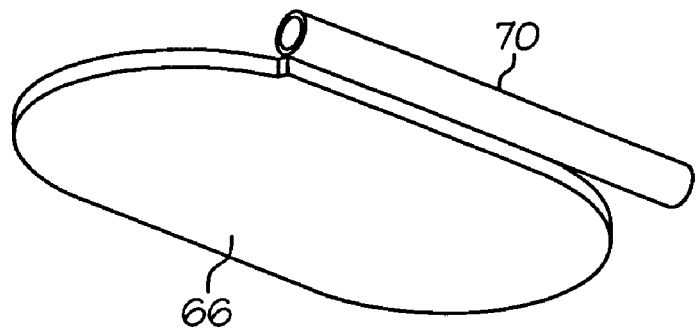
FIG. 14 is a perspective view of an exemplary embodiment of an electrode and crimp tube for electrically connecting a conductor wire with the electrode.
Figure 15:
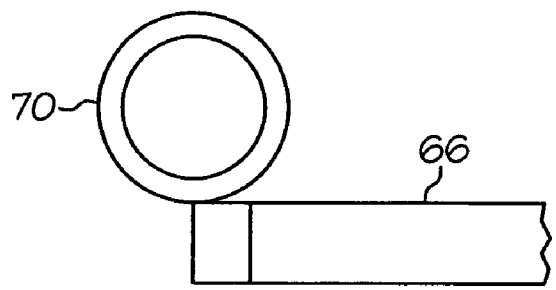
FIG. 15 is an end view of the electrode and crimp tube of FIG. 8.
Figure 16:
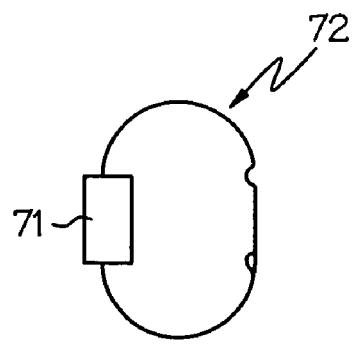
FIG. 16 is a back view of a second exemplary embodiment of an electrode with an integral crimp feature for connecting a conductor wire with the electrode.
Figure 17:
FIG. 17 is an end view of the exemplary electrode of FIG. 16.

Exemplary embodiments of the lead body 52 preferably includes a center strut 53 as illustrated in FIGS. 10 and 11 housed in an electrically insulative tubing or jacket, such as urethane tubing having a Shore D hardness of 55D, or pentalumen tubing 55 as illustrated FIGS. 12 and 13, which may also be housed in an electrically insulative tubing or jacket. The exemplary center strut defines a central stylet lumen and longitudinally extending channels for receiving conductor wires. The exemplary pentalumen tubing defines a central stylet lumen and a plurality (e.g., 4) of longitudinally extending conductor lumens arranged radially outwardly from the central stylet lumen.

Figure 9:
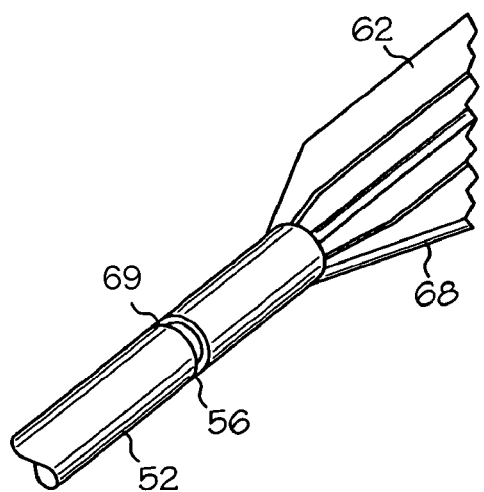
FIG. 9 is an exploded, partial view of the exemplary paddle-style medical lead of FIGS. 6-8, illustrating the location of a butt joint joining the paddle with the lead body.

The proximal end 68 of the flat paddle 62 preferably tapers down to the diameter of the lead body 52 as illustrated in FIGS. 4, 5, 6 and 8. FIG. 9 illustrates the butt joint 69 that may be used between the paddle 62 and the lead body 52 to minimize loading of electrical connections. The butt bond 69 may be formed, for example, with urethane adhesive.

Figure 7:
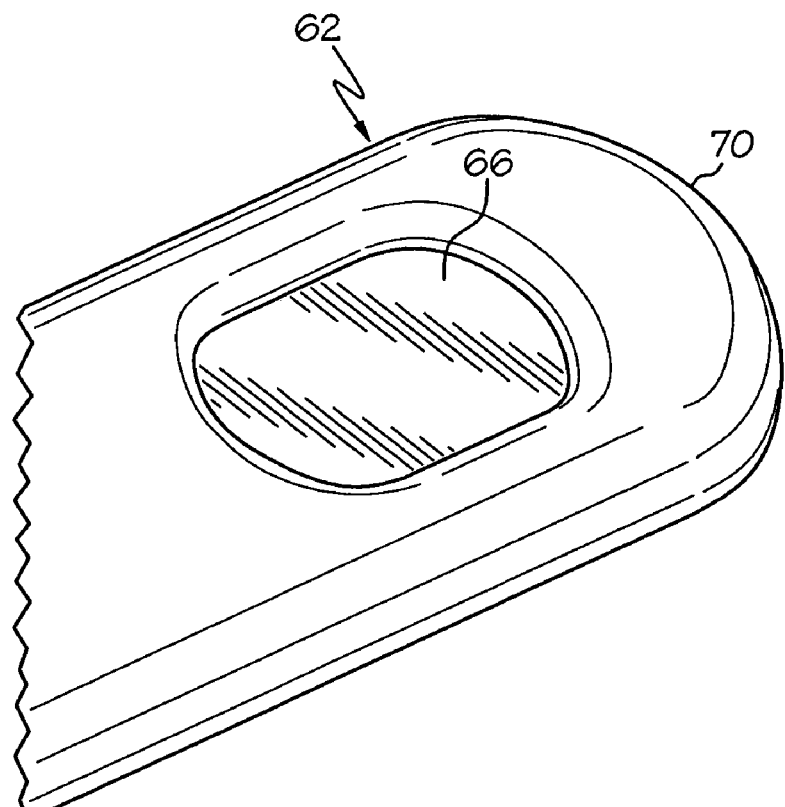
FIG. 7 is an enlarged view of a portion of the exemplary medical lead of FIG. 6, illustrating features of an exemplary electrode and paddle.
Figure 8:
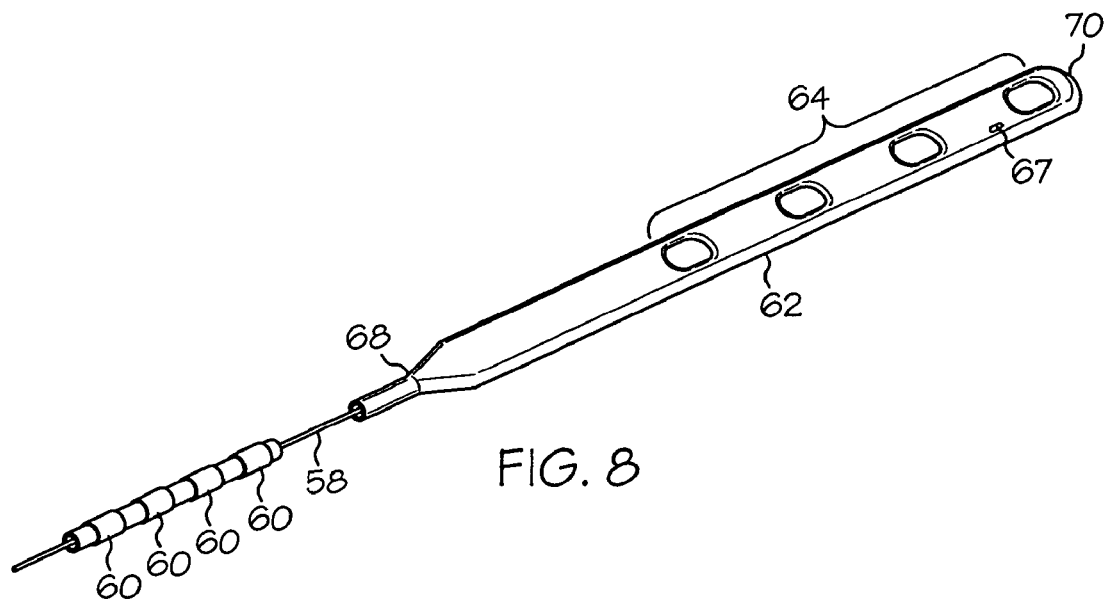
FIG. 8 is an exploded, partial view of the exemplary paddle-style medical lead of FIGS. 6 and 7.

The electrodes 66 may be recessed relative to the surface of the paddle as illustrated in FIG. 7, or co-planer with the surface. Examples include recessing the electrode 0.010 inches (0.25 mm) from the surface with the electrode having a surface area of approximately 6 mm$^2$.

An identification or orientation marker 67 (FIGS. 6 and 8) may be provided on the paddle 62 to indicate to physicians which side of the electrode plate is exposed versus insulated during and after implant. This may be helpful, for example, to determine whether the lead 50 has flipped or twisted during implantation. For example, an orientation marker 67 for determining orientation of the lead 50 may include fluoroscopically viewable material, such as radio-opaque material (e.g., platinum or platinum/iridium alloy). Since the electrode array 64 of at least one exemplary embodiment of medical lead comprises electrodes 66 exposed only through the first major surface of the paddle 62, the orientation marker 67 may be employed to provide a definite indication of the direction the paddle 62 (and electrode array 64) is facing.

For example, the paddle 62 may be considered as defining an imaginary longitudinal center line, and the orientation marker 67 may comprise a discrete radio-opaque marker displaced from the longitudinal center line. When fluoroscopically viewing an implanted medical lead, the orientation of the paddle 62 may be determined by noting on which side of the imaginary center line the orientation marker 67 appears to be positioned.

In an exemplary embodiment, the orientation marker may comprise radio-opaque material arranged in an asymmetric manner with respect to the width of the paddle. As an alternative example of this embodiment, the orientation marker may comprise radio-opaque material dispersed in the paddle in an asymmetric manner with respect to the width of the paddle. Such radio-opaque material may be dispersed, for example, substantially uniformly in an asymmetric portion arranged asymmetrically with respect to the width of the paddle. The orientation of the implanted paddle may be determined by viewing an apparent asymmetric position of the orientation marker on the paddle, and determining, based on the apparent asymmetric position of the orientation marker, which direction the paddle is facing.

In a preferred exemplary embodiment, the orientation marker 67 is coded to identify the model or serial number of the lead 50. The code would preferably be fluoroscopically visible after implantation of the lead 50.

FIGS. 14-17 illustrate alternative preferred exemplary embodiments of means for electrically connecting a conductor wire to the electrode. The exemplary embodiment of FIGS. 14 and 15 involve use of a connector 70 (e.g., crimp tube 70), which is crimped to the conductor and welded, e.g., laser welded) to the lateral edge of the electrode 66. The exemplary embodiment of FIGS. 16 and 17 involves a crimp connector 71 that is an integral part of the electrode 72. The crimp connector 71 is shown in the form of a tab (also 71) that may be bent or crimped to connect the conductor to the electrode 72.

The exemplary embodiments of the connection means illustrated in FIGS. 14-17 are adapted to have strain or tension relief properties if the conductors are put under tension. Each of these means are illustrated as connecting the conductor to the lateral edge of the electrode 66 or 72 (relative to the longitudinal centerline of the paddle) such that tension along the conductor would tend to spin the electrode 66 or 72 thus tending to relieve such tension.

Figure 18:
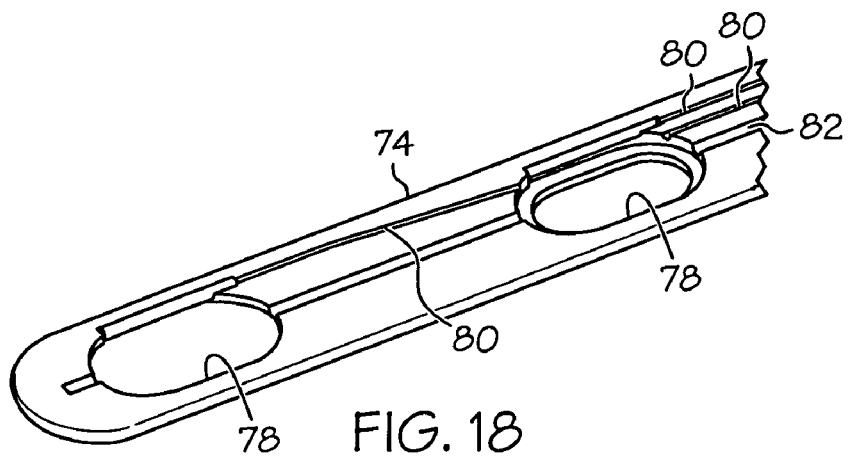
FIG. 18 is a perspective view of a half portion of an exemplary embodiment of the paddle, illustrating the connection of a conductor wire to the electrode via a crimp tube arranged along a lateral side of the electrode, the arrangement being such that tension tends to turn the electrode thus providing some additional strain relief.
Figure 19:
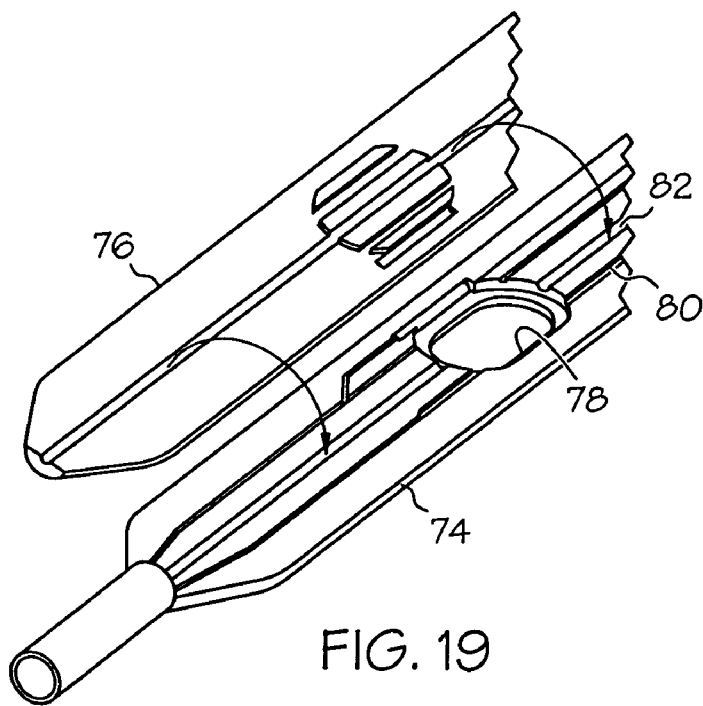
FIG. 19 is a perspective view of two half portions of an exemplary embodiment of the paddle, illustrating aspects of assembly of the paddle.
Figure 20:
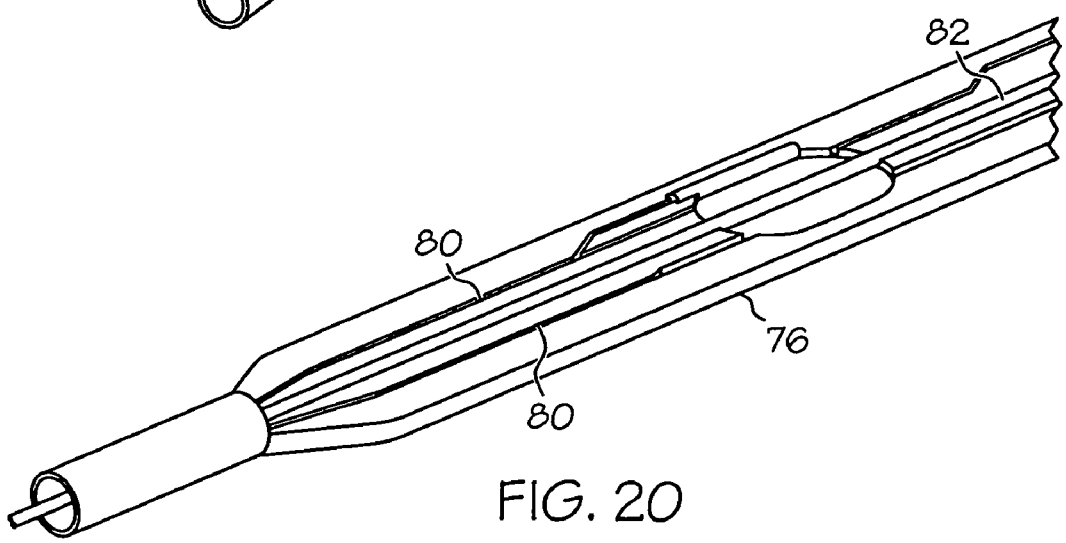
FIG. 20 is a perspective view of the paddle with one half portion removed to illustrate passage of a stylet.

The paddle 62 may be formed of two half sections 74 and 76 (e.g., "lower" paddle half 74 and "upper" paddle half 76) as shown on FIGS. 18-20. For example, the half sections 70 and 72 may be formed of polyurethane. Electrode receiving apertures 78 may be provided (e.g., molded) in the lower paddle half 74. Conductor wire paths 80 and stylet-lumen-forming channels 82 may be formed (e.g., molded) in one of both of the lower and upper paddle halves 74 and 76.

The sections 74 and 76 are bonded together (e.g., with polyurethane adhesive) after assembly and connection (e.g., laser welding and/or crimping) of the electrodes 66 and conductors. The stylet-lumen forming channels 82 thus form a stylet lumen.

Figure 21:
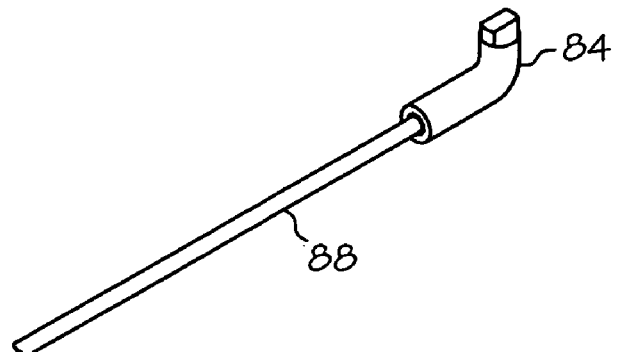
FIG. 21 is a perspective view of an exemplary embodiment of a conductor and crimp sleeve for use in connecting to a proximal contact.
Figure 22:
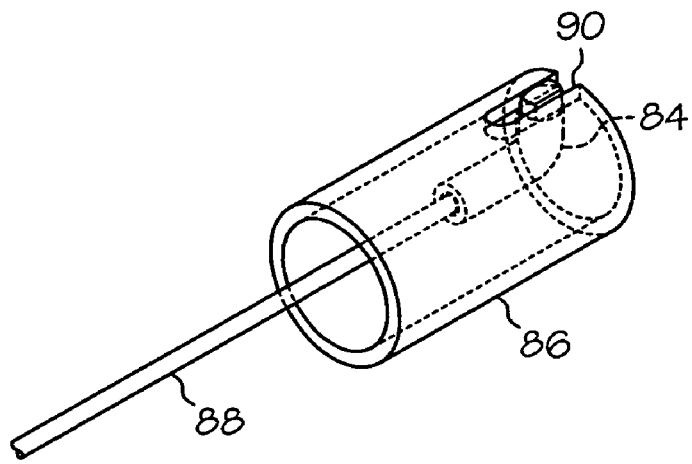
FIG. 22 is a perspective view of an exemplary embodiment of a conductor and crimp sleeve of FIG. 13 shown in relation with an exemplary proximal contact.

FIGS. 21 and 22 illustrate aspects of an exemplary embodiment of a crimp sleeve 84 for electrically connecting the proximal contacts 86 (e.g., contact ring) and conductor wires 88. A miniature conductor 88 is crimped to the sleeve 84, and the proximal contact 86 includes a slot 90 for receiving the crimp sleeve 84. In at least one example, the sleeve 84 is then bent and its end flattened to match the slot 90 in the contact 86, and the crimped cable/sleeve assembly is welded to the contact 86.

Figure 23:
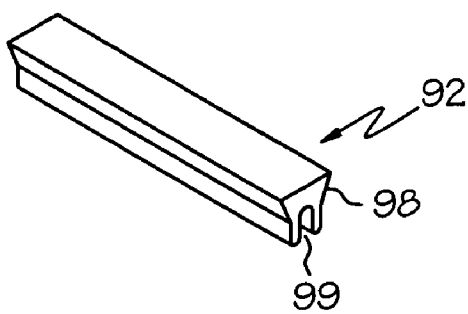
FIG. 23 is a perspective view of a second exemplary embodiment of a crimp sleeve for use in connecting a conductor to a proximal contact.
Figure 24:
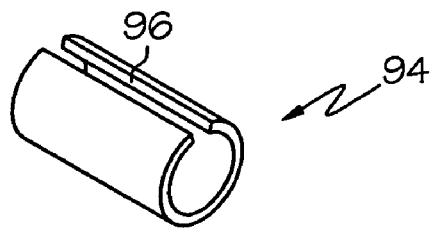
FIG. 24 is a perspective view of a second exemplary embodiment of a proximal contact for use with the exemplary crimp sleeve of FIG. 23.

FIGS. 23 and 24 illustrate aspects of a second preferred exemplary embodiment of a crimp sleeve 92 and proximal contact ring 94. The contact ring 94 is generally cylindrical and has a longitudinal slot 96 for receiving the flared contact-connecting portion 98 of the crimp sleeve 92, which may be welded, for example, in place. The crimp sleeve includes a conductor-wire-receiving channel 99, which may be crimped to retain the conductor wire. Exemplary alternatives to the channel 99 include without limitation a crimp-able lumen (not shown).

Figure 25:
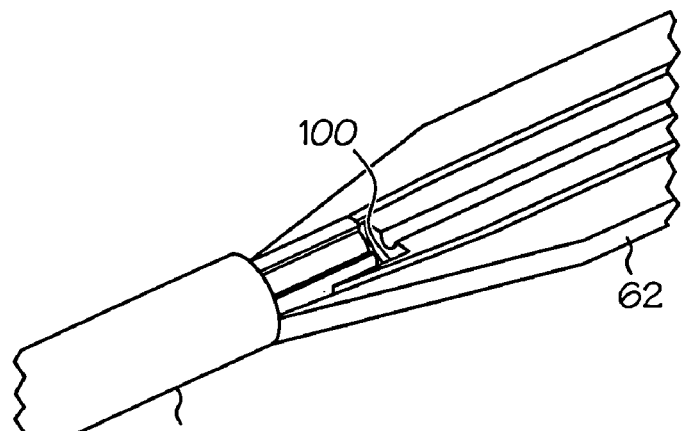
FIGS. 25 and 26 are perspective views of an exemplary embodiments of a proximal area of a lead and the interface between the lead body and lead paddle, illustrating location of adhesive to minimize tensile loading of electrical conductors, contacts and electrodes.
Figure 26:
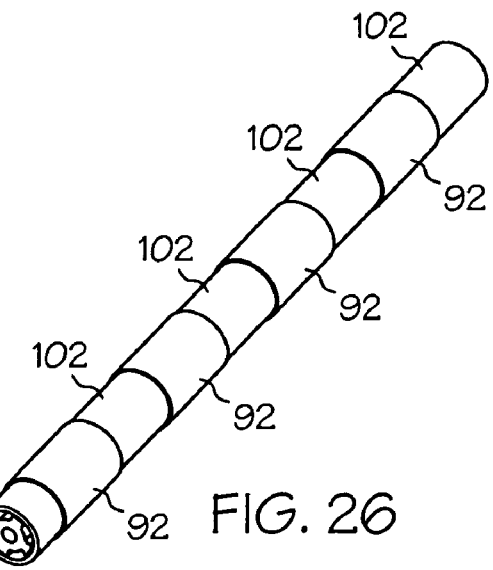
Figure 27:
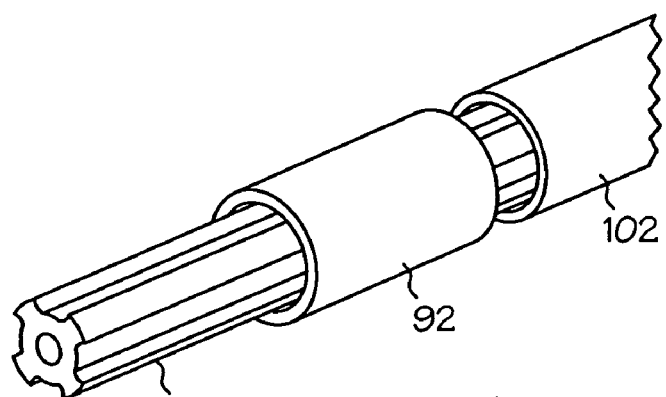
FIG. 27 is a perspective view illustrating an exemplary embodiment of the assembly of a proximal contact on an exemplary embodiment of a center strut of a lead.

FIG. 25 illustrates an example of where (e.g., at 100) the center strut 53 may be adhesively bonded to the proximal end of the paddle 62 (e.g., with urethane adhesive). FIG. 27 illustrates the distal end 56 of the body portion 52, which is bonded to the proximal end of the paddle at 100 in FIG. 25. As illustrated at 100 in FIG. 25, for example, the joint may be formed between the paddle 62 and the center strut 53 and/or the electrically insulative tubing or jacket in the center strut or strut composite embodiment of the lead body. The adhesive bond 100 in FIG. 25 may constitute more than a butt bond in that the center strut 53 may be adhesively received in the paddle. The strut composite embodiment, and bonding the center strut 53 to the proximal end of the paddle 62, are particularly adapted to protect the electrical connections from tensile loading.

Figure 28:
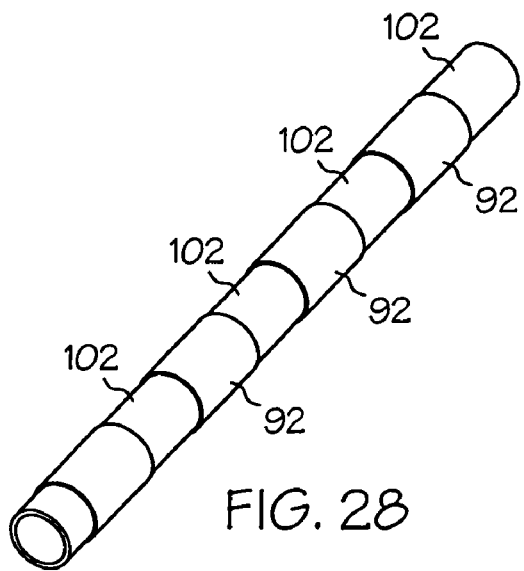
FIG. 28 is a perspective view illustrating electrically conductive proximal contacts separated by electrically insulative spacers.
Figure 29:
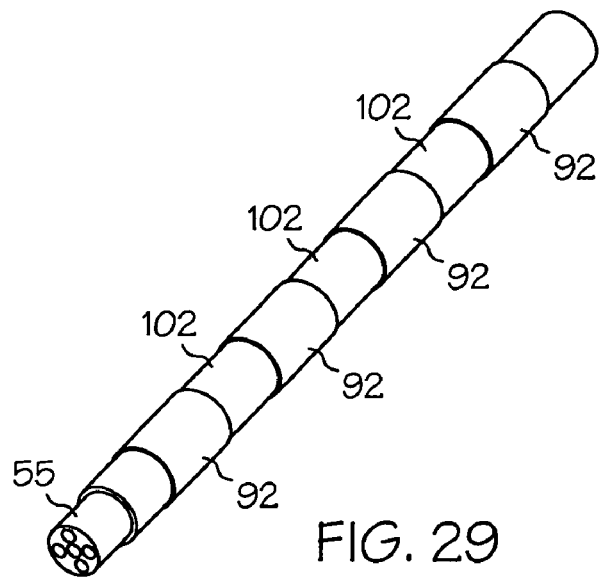
FIG. 29 is a perspective view illustrating electrically conductive proximal contacts separated by electrically insulative spacers arranged on pentalumen tubing.
Figure 30:
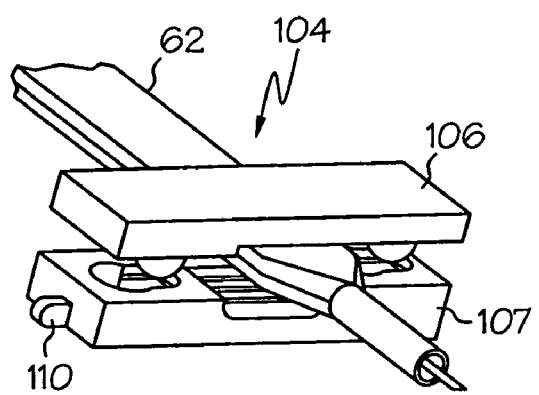
FIG. 30-33 are perspective views of an exemplary embodiment of an anchor for use with exemplary embodiments of the medical lead.
Figure 31:
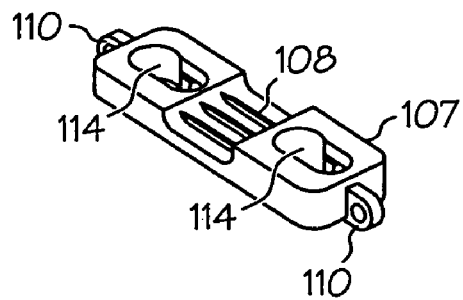
Figure 32:
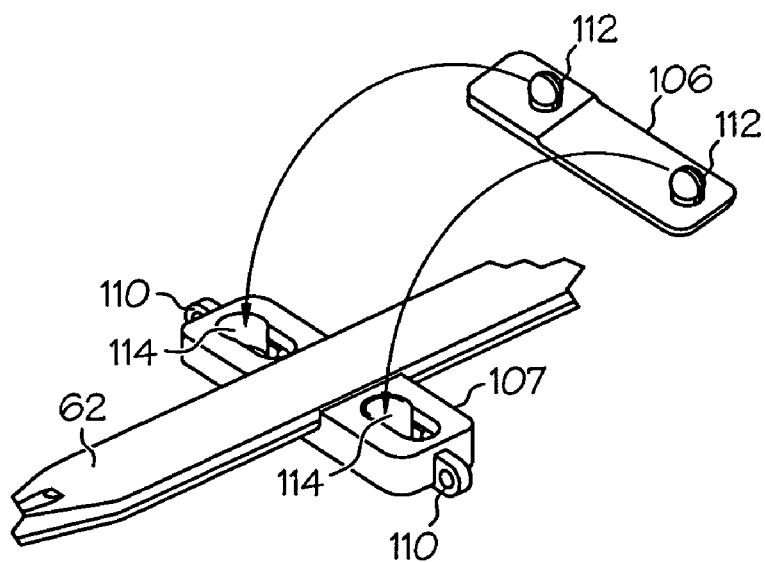
Figure 33:
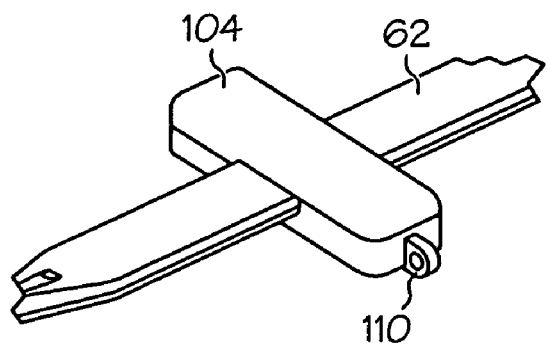

FIGS. 27-29 illustrate various exemplary details of the proximal contact portion and the assembly thereof. For example, FIG. 27 illustrates assembly of proximal contacts 92 on a center strut 53 alternating with assembly of an electrically insulative urethane spacer 102. FIG. 29 illustrates an exemplary arrangement of proximal contacts 92 and urethane spacer 102 arranged on a pentalumen tube 55.

An anchor, such as the anchor 104 illustrated in FIGS. 30-33, may be provided for clamping the flat paddle 62 and anchoring it to connective tissue, such as the ligamentum flavum 30. For example, two clamping jaws 106 and 107 of the anchor 104 are adapted to clamp the major surfaces of the flat paddle 62. One or both of the clamping arms 106 or 107 may be provided with at least one rib, but preferably a plurality of ribs 108 (e.g., 3), adapted to engage the flat paddle 62 and retain it in position. Suture loops 110 may be provided to suture the anchor 104 to connective tissue. The clamping arms 106 and 107 are preferably separable, with the clamping arms 106 and 107 being provided with mating knobs 112 and cavities 114 or other features for attaching the clamping arms 106 and 107 together.

Figure 34:
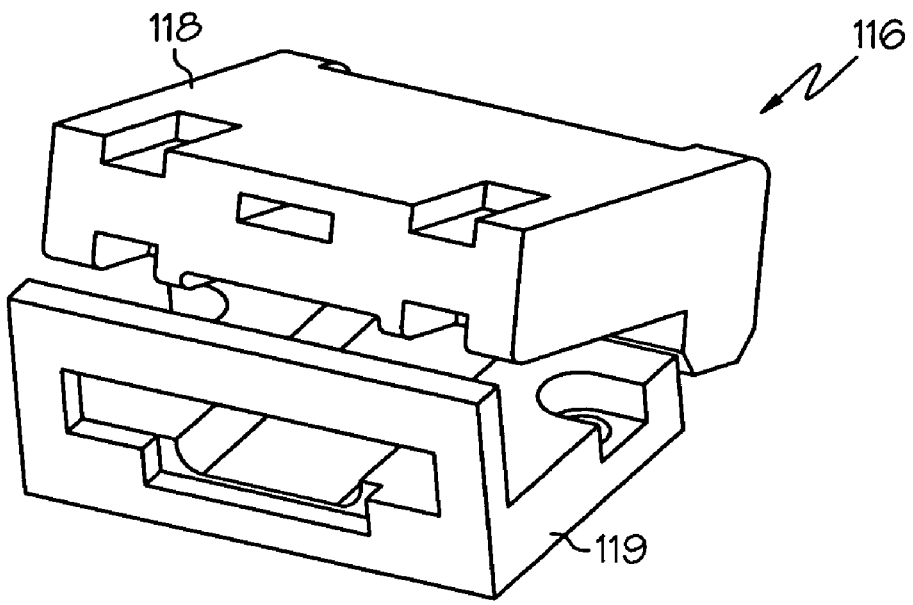
FIGS. 34 and 35 are perspective views of additional exemplary embodiments of an anchor for use with exemplary embodiments of the medical lead.
Figure 35:
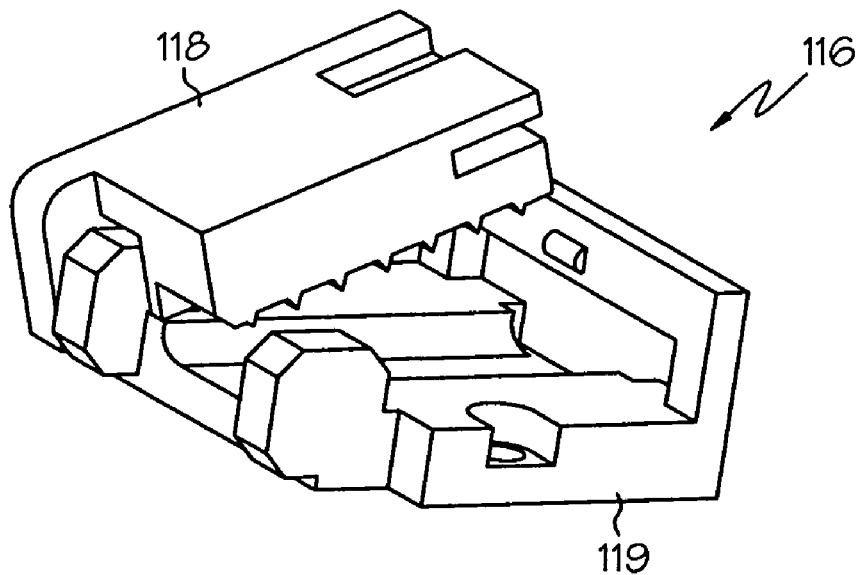

FIGS. 34 and 35 illustrate alternative exemplary embodiments of an anchor 116 in which the halves or jaws 118 and 119 pivot relative to one another in a clam shell fashion to anchor the lead 50. This embodiment may employ mating knobs and ribs as discussed with respect to the embodiment of FIGS. 30-33.

Figure 36:
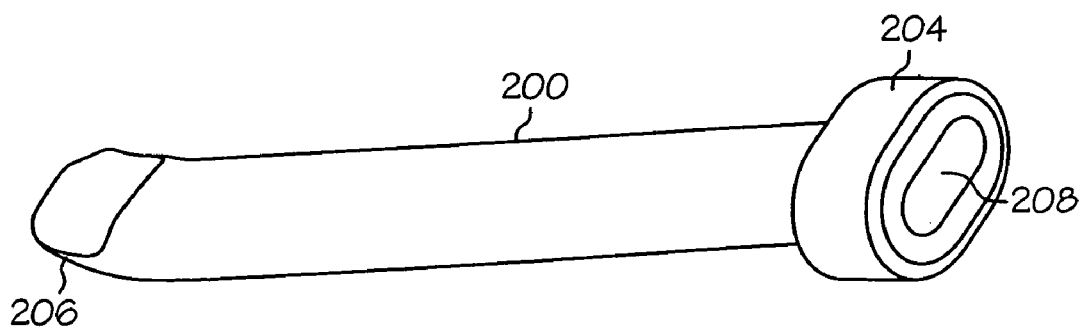
FIG. 36 is a perspective view of an exemplary embodiment of a needle, which has a flattened or oblong cross section for insertion of exemplary embodiments of the medical lead.
Figure 37:
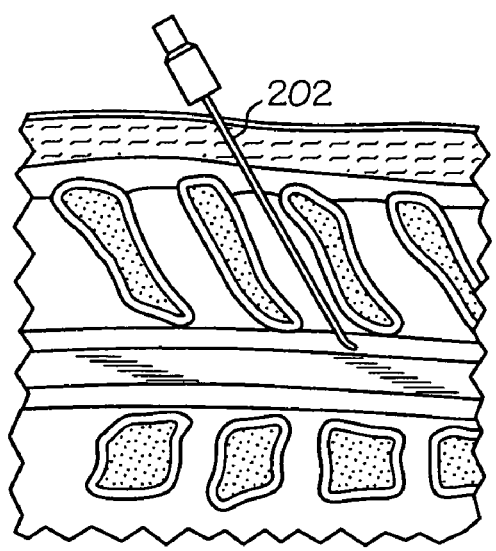
FIG. 37 is a vertical cross section view along a sagittal plane illustrating use of the needle of FIG. 36 to place a lead epidurally.
Figure 38:
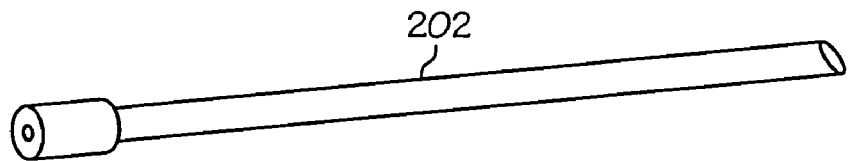
FIG. 38 is a perspective view illustrating an exemplary embodiment of a stylet for use in the oblong needle of FIGS. 36 and 37.

FIGS. 36-38 illustrate a preferred embodiment of a needle 200 and stylet 202 for use in exemplary embodiments of a procedure for introducing a paddle style lead 50 within the spinal column area, such as the epidural area, as depicted in FIG. 37. Alternative exemplary embodiments may into or near other nervous system structures, central or peripheral, such as intracranial nervous system structures or peripheral nerves.

As illustrated in FIG. 37, the needle assembly may be inserted into the spinal column area (e.g., epidurally). In an exemplary embodiment of the needle assembly, the lumen of the needle 200 has an oblong cross section sized to insert a paddle style lead 50 and has a curve at the distal end of the needle 200. U.S. Pat. Nos. 6,249,707 and 6,309,401, and EP 1 048 270, are incorporated herein by reference in their entirety, and particular note is made of the flattened needle, which may be used with certain exemplary embodiments of the medical lead disclosed herein.

The needle 200 comprises a body having a proximal end 204 and a distal end 206 and an inside lumen 208. The lumen 208 has an oblong cross section. The oblong cross section of the lumen 208 is adapted to receive a stylet 202 (FIG. 30) and a paddle style lead 50. The cross section of the lumen 208 is such that the width is greater than the height. A typical width for the lumen cavity to receive a paddle style lead 50 may be 2.5 mm to 12 mm (0.1" to 0.5") with a height of 1.4 mm to 2.0 mm (0.055" to 0.079"). The needle 200 may be made of stainless steel or other suitable materials. The needle 200 may also be adapted to insert multiple wire leads. Advantageously, the present invention allows a paddle lead to be inserted percutaneously without requiring the lead 50 to be rolled/contorted to fit the geometry of the needle lumen 208.

The needle 200 is further defined by an introducer portion (also 206) at the body distal end 206. The introducer portion 206 has a top side and a bottom side is shaped to allow for penetration of a patient's skin and other tissue. Typically, an epidural, Tuohy or modified Tuohy needle may be used. The top side of the introducer portion 206 has an orifice to allow the paddle style lead 50 to exit the lumen 208 of the needle 200 within the spinal column area after insertion of the needle 200. The introducer portion 206 may have the orifice at the distal end perpendicular to the lumen 208. A preferred exemplary embodiment of the needle 200 has an introducer with a curvature. The curvature extends from the bottom side of the introducer 206 to the top side of the introducer to facilitate and guide the paddle style lead 50 during insertion. The radius of curvature for the introducer 206 may be, for example, approximately 0.9". Other curvatures may also be used.

FIG. 38 illustrates a perspective view of the stylet 202 having a proximal end that is adapted to mate with the needle hub. The stylet 202 has a length nearly equivalent to the length of the body of the needle 200. The stylet 202 has a distal tip shaped for matching with the orifice of the introducer of the needle 200. A handle end is affixed to a proximal end of the stylet 202. In the preferred embodiment, the stylet 202 fills the entire orifice of the introducer 206 to prevent any skin or other tissue from entering the lumen 208 during insertion within the patient.

In at least one preferred exemplary embodiment, the stylet 202 may be constructed of an elastomeric material, or deformable material that is sufficiently flexible and resilient or redeformable to allow the stylet 202 to be removed from the needle 200 even where the needle 200 has been subjected to plastic deformation. Alternatively, the stylet 202 may be formed of stainless steel.

Figure 39:
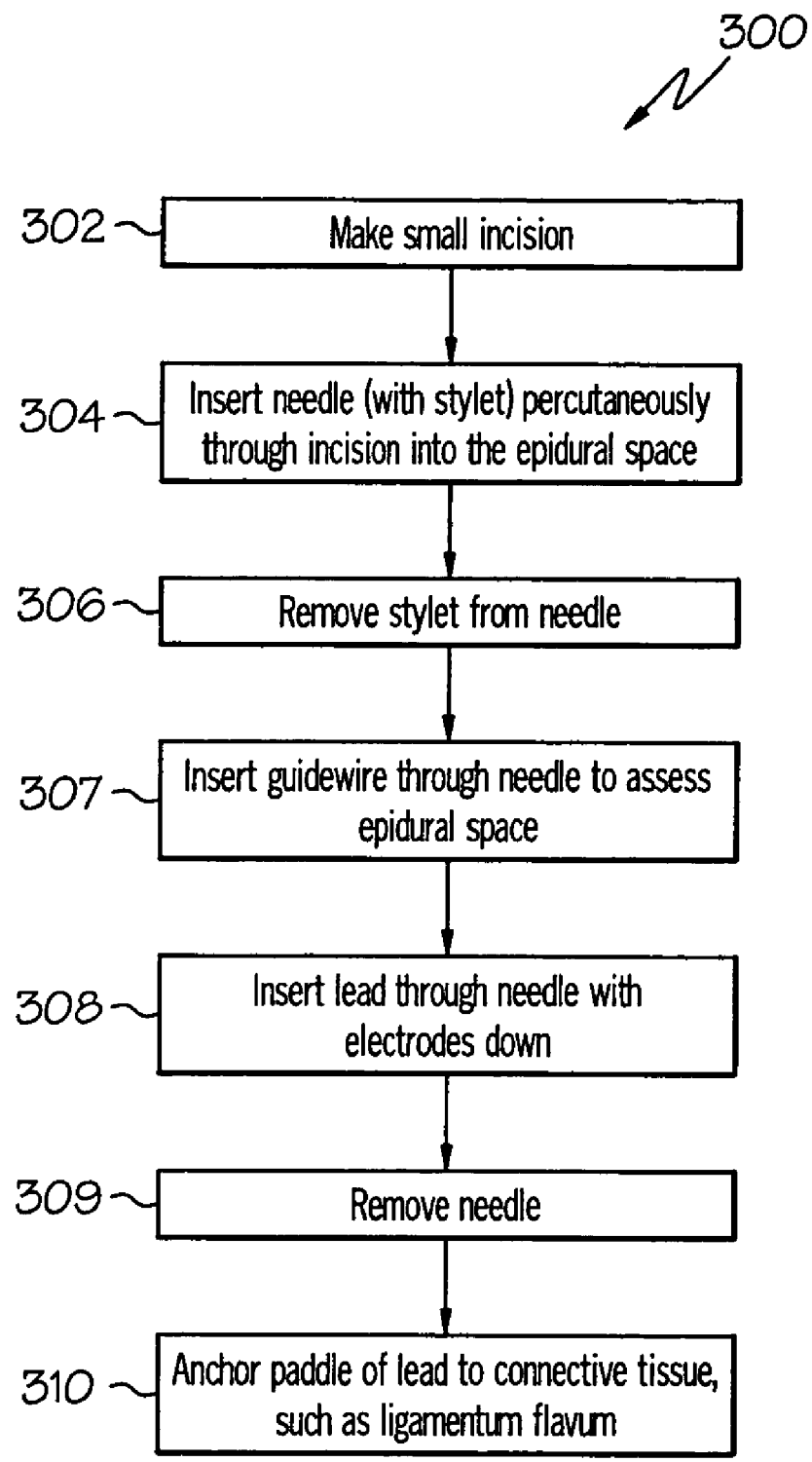
FIG. 39 is a flow chart illustrating an exemplary embodiment of a method of percutaneously implanting a medical lead.

FIG. 39 illustrates a general flow diagram of an exemplary preferred method 300 of use or implantation of the implantable paddle-style medical lead 50. The method 300 generally follows these steps: make small incision 302; insert needle (with stylet) percutaneously through incision into the epidural space 304; remove stylet from needle 306; insert guidewire through needle to assess epidural space 307; insert lead through needle with electrodes down 308; remove needle 309; and anchor paddle of lead to connective tissue, such as ligamentum flavum 310.

Figure 40:
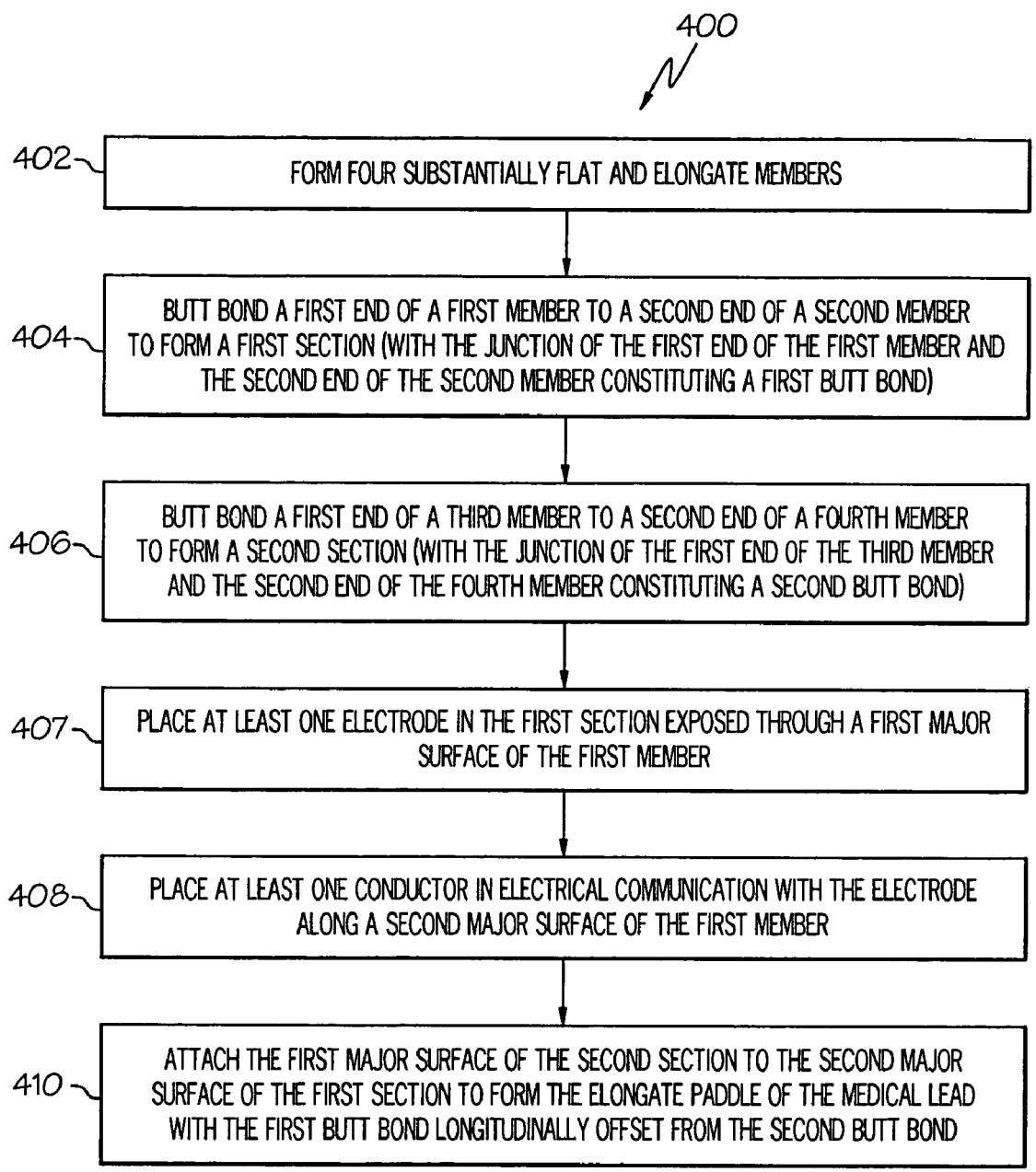
FIG. 40 is a flow chart illustrating an exemplary embodiment of a method of making a paddle-style medical lead.
Figure 41:
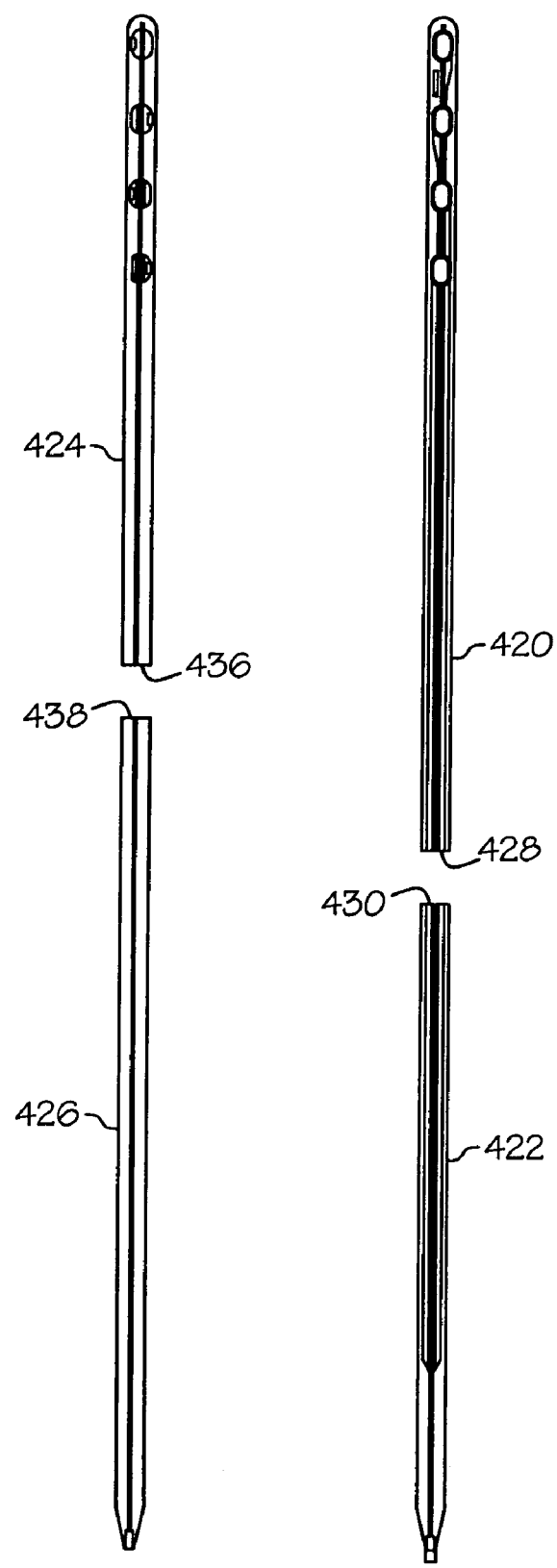
FIG. 41 is a top plan view of an exemplary embodiment of four elongate members that may be used to form a paddle in an exemplary manufacturing method embodiment.
Figure 42:
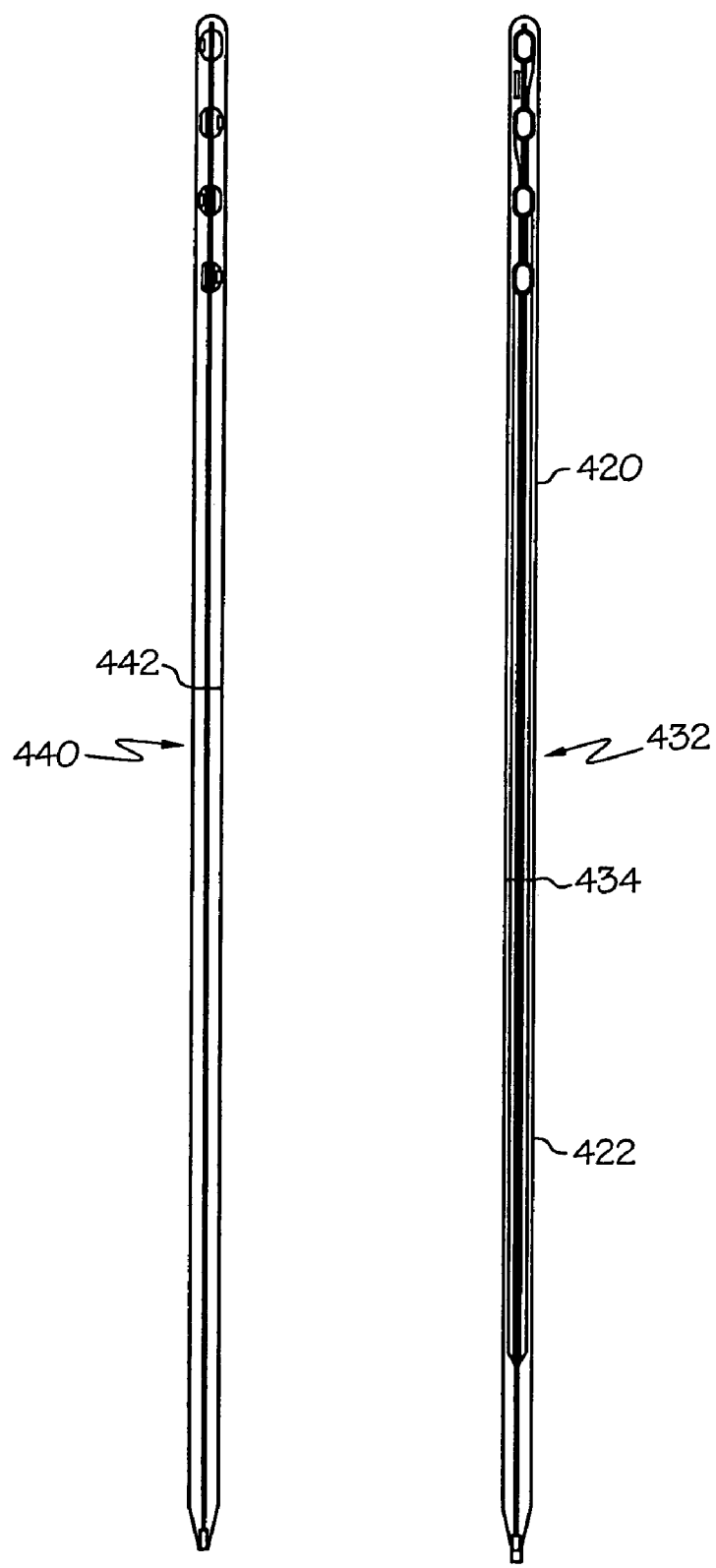
FIG. 42 is a top plan view of the exemplary embodiment of FIG. 41, showing a first and second elongate member butt bonded together and a third and fourth elongate member butt bonded together.
Figure 43:
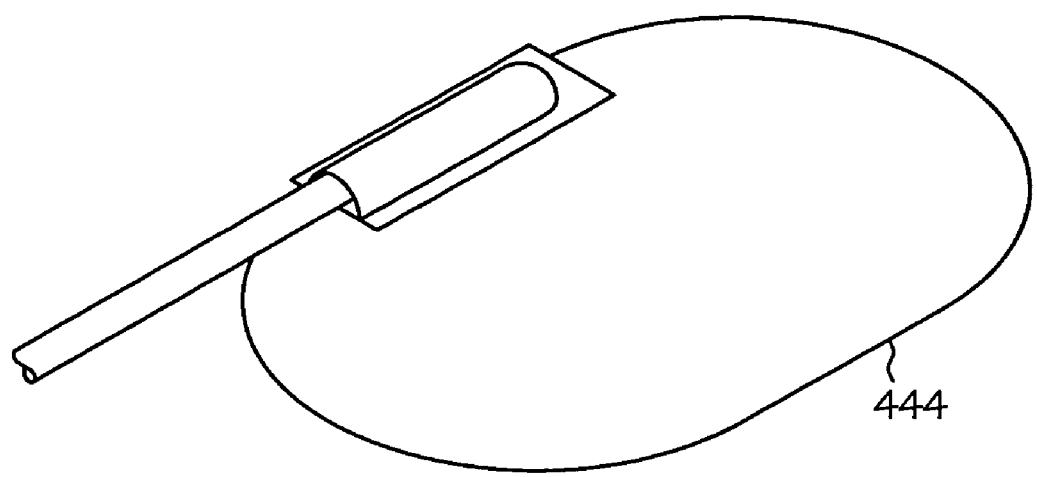
FIG. 43 illustrates an exemplary step in the manufacturing method in which a conductor is connected to the lateral edge of an electrode.

FIG. 40 illustrates an exemplary embodiment of a method 400 of manufacturing a medical lead. The method 400 of this embodiment generally comprises: (a) forming at least first, second, third and fourth substantially flat and elongate members 420, 422, 424 and 426 (FIG. 41), each member having first and second ends, as discussed at step 402; (b) butt bonding the first end 428 of the first member 420 to the second end 430 of the second member 422 to form a first section 432 (FIG. 42) with the junction of the first end 428 of the first member 420 and the second end 430 of the second member 422 constituting a first butt bond 434, the first section having first and second major surfaces, as discussed at step 404; (c) butt bonding the first end 436 of the third member 424 to the second end 438 of the fourth member 426 to form a second section 440 (FIG. 42) with the junction of the first end 436 of the third member 424 and the second end 438 of the fourth member 426 constituting a second butt bond 442, the second section 440 having first and second major surfaces, as discussed at step 406; (d) placing at least one electrode 444 in the first section 432 exposed through the first major surface of the first member 432 (FIG. 44), as discussed at step 407, and placing at least one conductor 446 in electrical communication with the electrode 444 along the second major surface of the first section 432, as discussed at step 408; and (e) attaching the first major surface of the second section 440 to the second major surface of the first section 432 to form the elongate paddle of the medical lead with the first butt bond 434 longitudinally offset from the second butt bond 442, as discussed at step 410. This offset may also be seen by comparing the longitudinal location of butt bonds 434 and 442 in FIG. 42.

In step (e), for example, the first major surface of the second section 440 may be adhesively bonded to the second major surface of the first section 432. As a more specific example, the first, second, third and fourth substantially flat and elongate members may be formed (e.g., molded) of material selected from the group consisting of urethane and polyurethane, the first major surface of the second section may be adhesively bond to the second major surface of the first section with urethane adhesive. Alternatively, the major surfaces may be bonded without the use of adhesive by directly bonding the first and second sections together. For example, such direct bonding may involve first and second sections that are laminated together before they have been completely cured.

Figure 44:
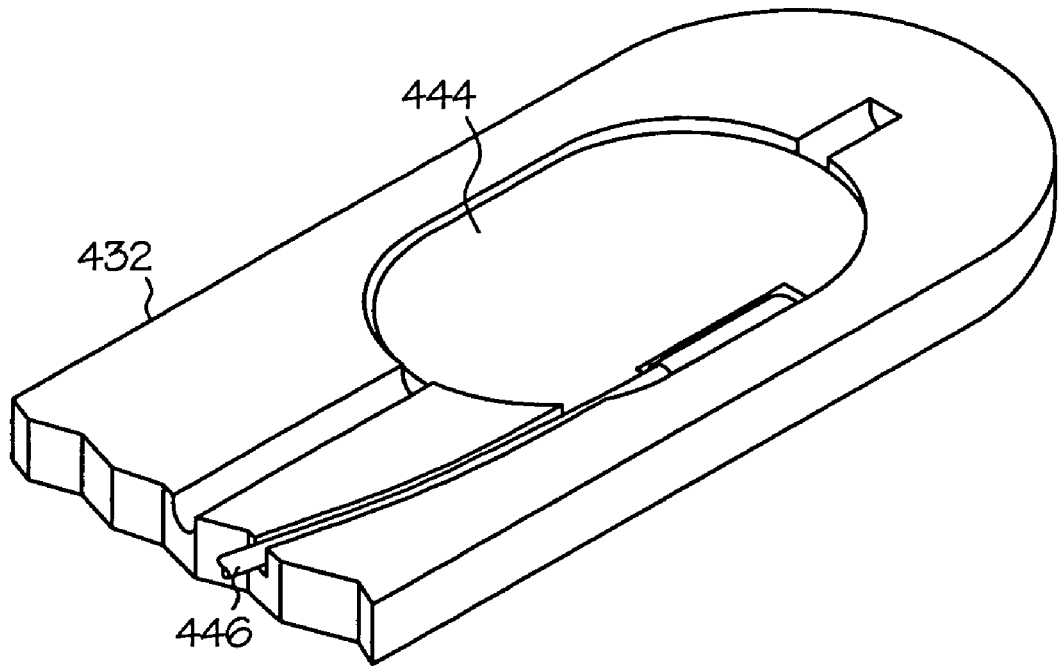
FIG. 44 illustrates an exemplary step in the manufacturing method in which an electrode is placed in an aperture in a first section and a conductor is placed in a path formed in the first section.
Figure 45:
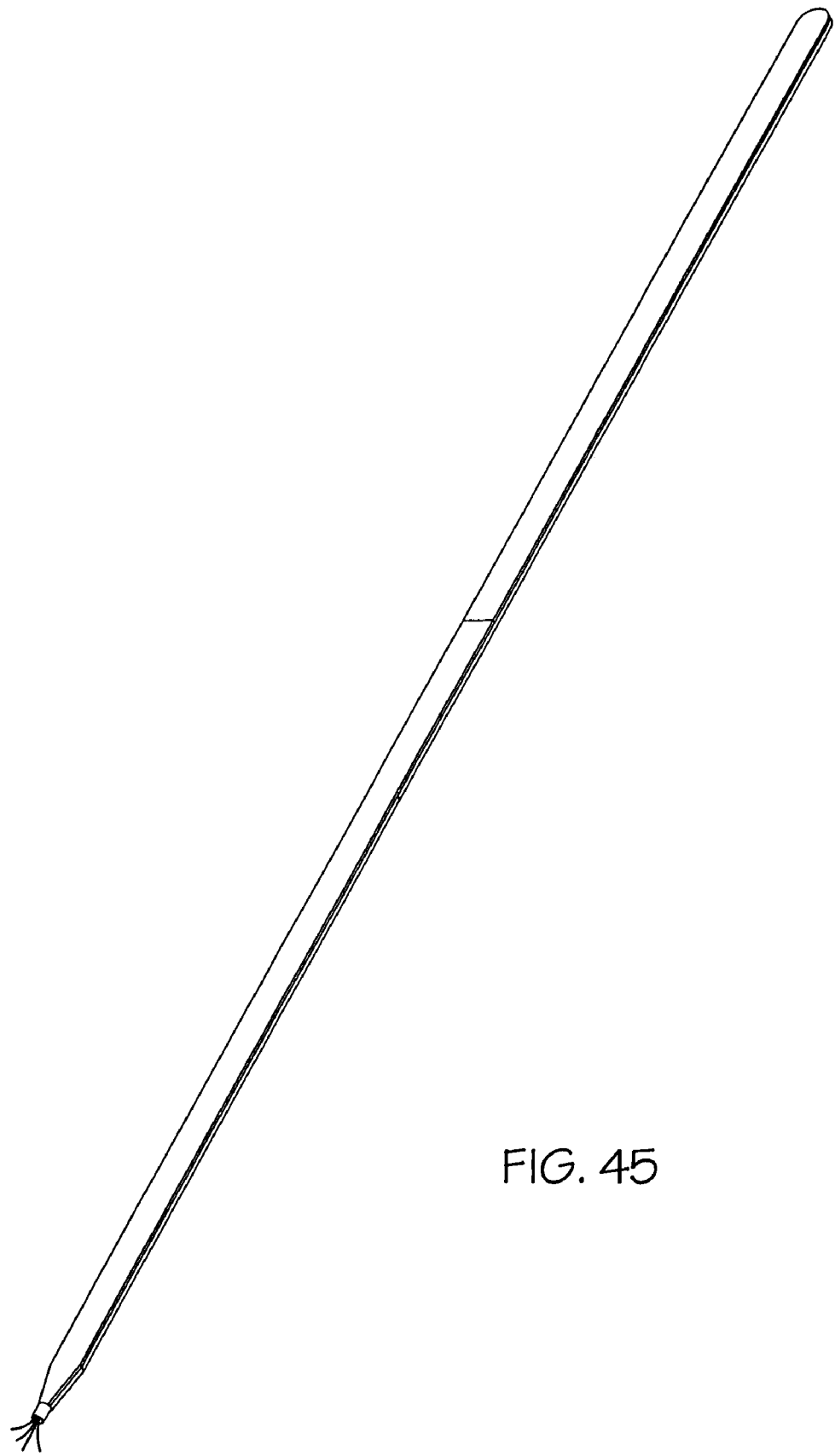
FIG. 45 illustrates an exemplary paddle made by an exemplary method.

Also, the first and second members may be molded with at least one aperture into at least one of the first and second members for receipt of an electrode and a path for receipt of at least one conductor. The electrode 444 is exposed through the first major surface of the first member 432 by placing the electrode in the aperture. The conductor-receiving path is arranged along the first and second members 420 and 422, such that when the first and second members are butt bonded to form the first section 432, the path is arranged along the second major surface of the first section 432. The conductor 446 may be placed in the path, as illustrated in FIG. 44.

The paddle defines a longitudinal center line, and the electrodes 444 have at least one lateral edge laterally offset from the center line. The conductor 446 is connected to the lateral edge of the electrode 444 such that tension along the conductor 446 would tend to torque the electrode 444 to relieve such tension. For example, the conductor may be connected to the lateral edge of the electrode by forming a connector, crimping the connector to the conductor and welding the connector to the lateral edge of the electrode.

Another exemplary step involves molding into each member 420, 422, 424 and 426 with a half channel arranged along each such that when the first and section sections 432 and 440 are attached to form a paddle the half channels form a stylet lumen.

An exemplary alternative embodiment of the manufacturing method involves extruding the first, second, third and fourth substantially flat and elongate members.

Figure 46:
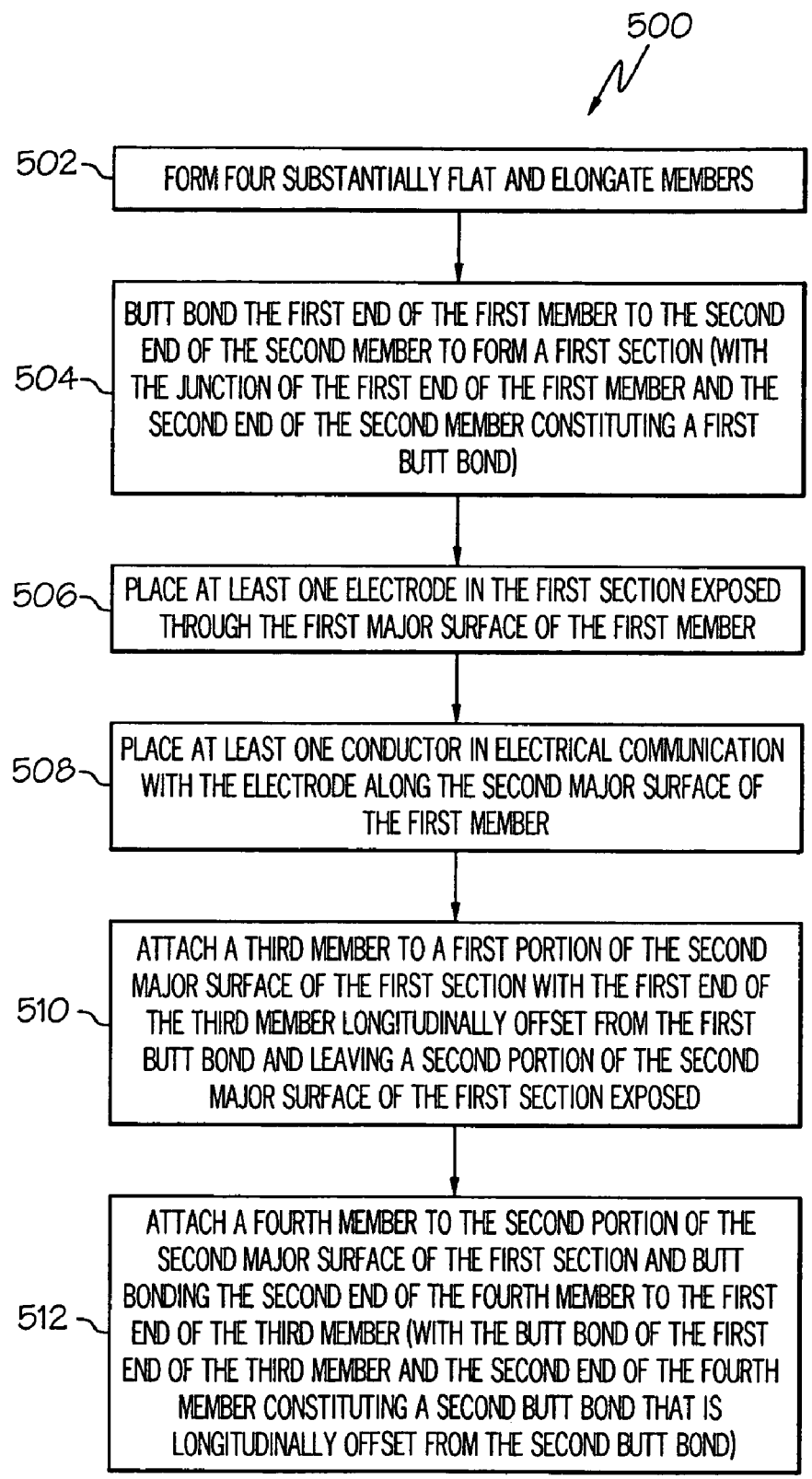
FIGS. 46-49 are flow charts illustrating exemplary embodiments of making medical leads.

In a second exemplary embodiment of the method of manufacturing a medical lead, the method 500 comprises (a) forming at least first, second, third and fourth substantially flat and elongate members, each member having first and second ends (step 502 in FIG. 46); (b) butt bonding the first end of the first member to the second end of the second member to form a first section with the junction of the first end of the first member and the second end of the second member constituting a first butt bond, the first section having first and second major surfaces (step 504 in FIG. 46); (c) placing at least one electrode in the first section exposed through the first major surface of the first member (step 506 in FIG. 46), and placing at least one conductor in electrical communication with the electrode along the second major surface of the first member (step 508 in FIG. 46); (d) attaching the third member to a first portion of the second major surface of the first section with the first end of the third member longitudinally offset from the first butt bond and leaving a second portion of the second major surface of the first section exposed (step 510 in FIG. 46); and attaching the fourth member to the second portion of the second major surface of the first section and butt bonding the second end of the fourth member to the first end of the third member with the butt bond of the first end of the third member and the second end of the fourth member constituting a second butt bond, and thus forming the elongate paddle of the medical lead with the first butt bond longitudinally offset from the second butt bond (step 512 in FIG. 46).

Figure 47:
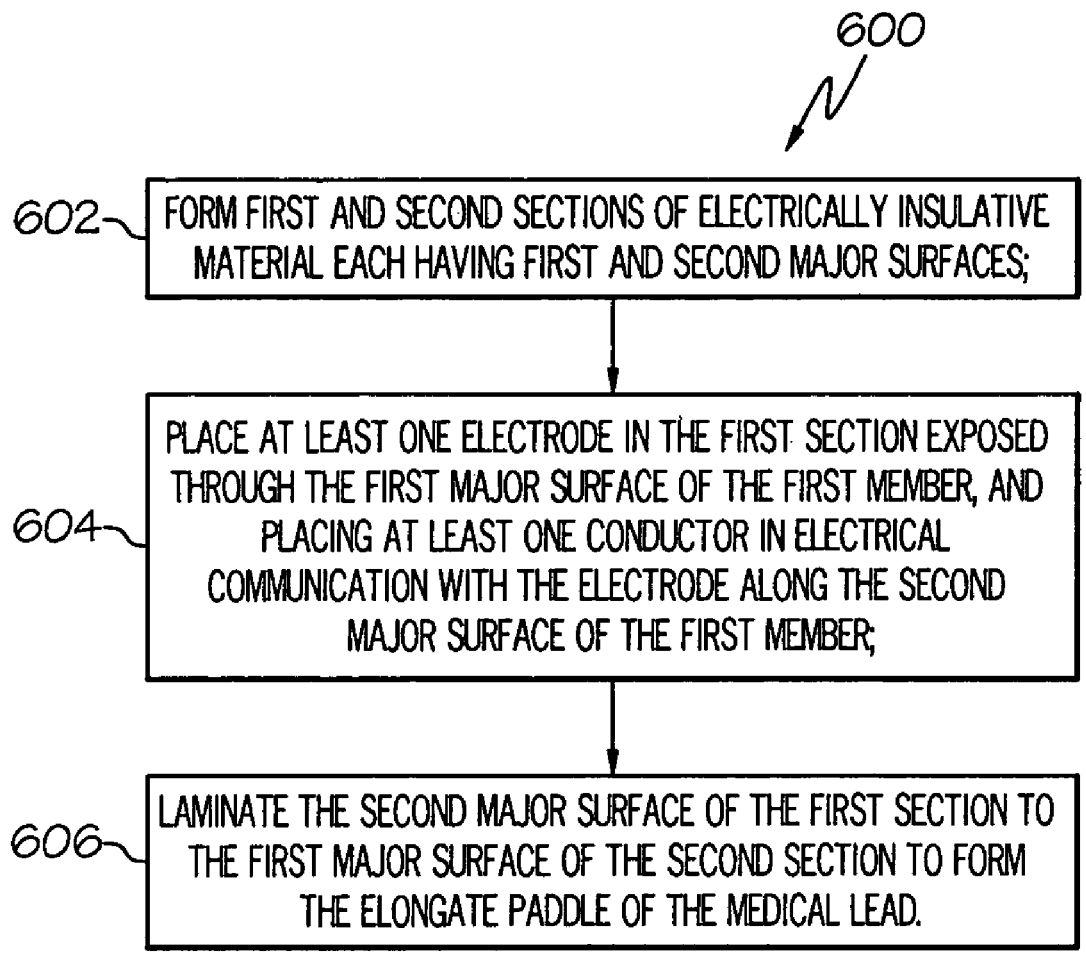

In a third exemplary embodiment of a method of manufacturing a medical lead, the method 600 comprises (a) forming first and second sections of electrically insulative material each having first and second major surfaces (step 602 in FIG. 47); (b) placing at least one electrode in the first section exposed through the first major surface of the first member, and placing at least one conductor in electrical communication with the electrode along the second major surface of the first member (step 604 of FIG. 47); and (c) laminating the second major surface of the first section to the first major surface of the second section to form the elongate paddle of the medical lead (step 606 of FIG. 47).

Figure 48:
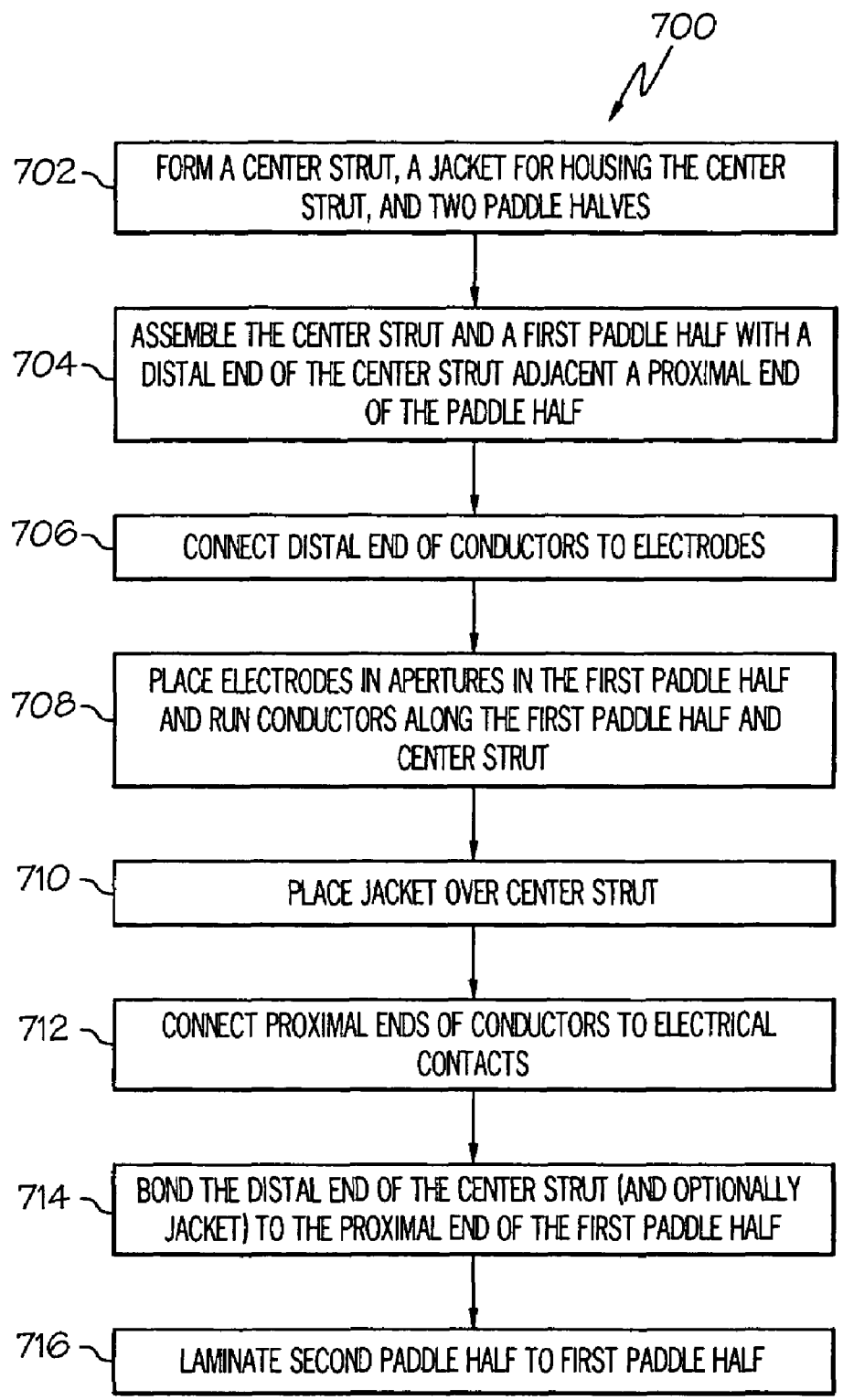
Figure 49:
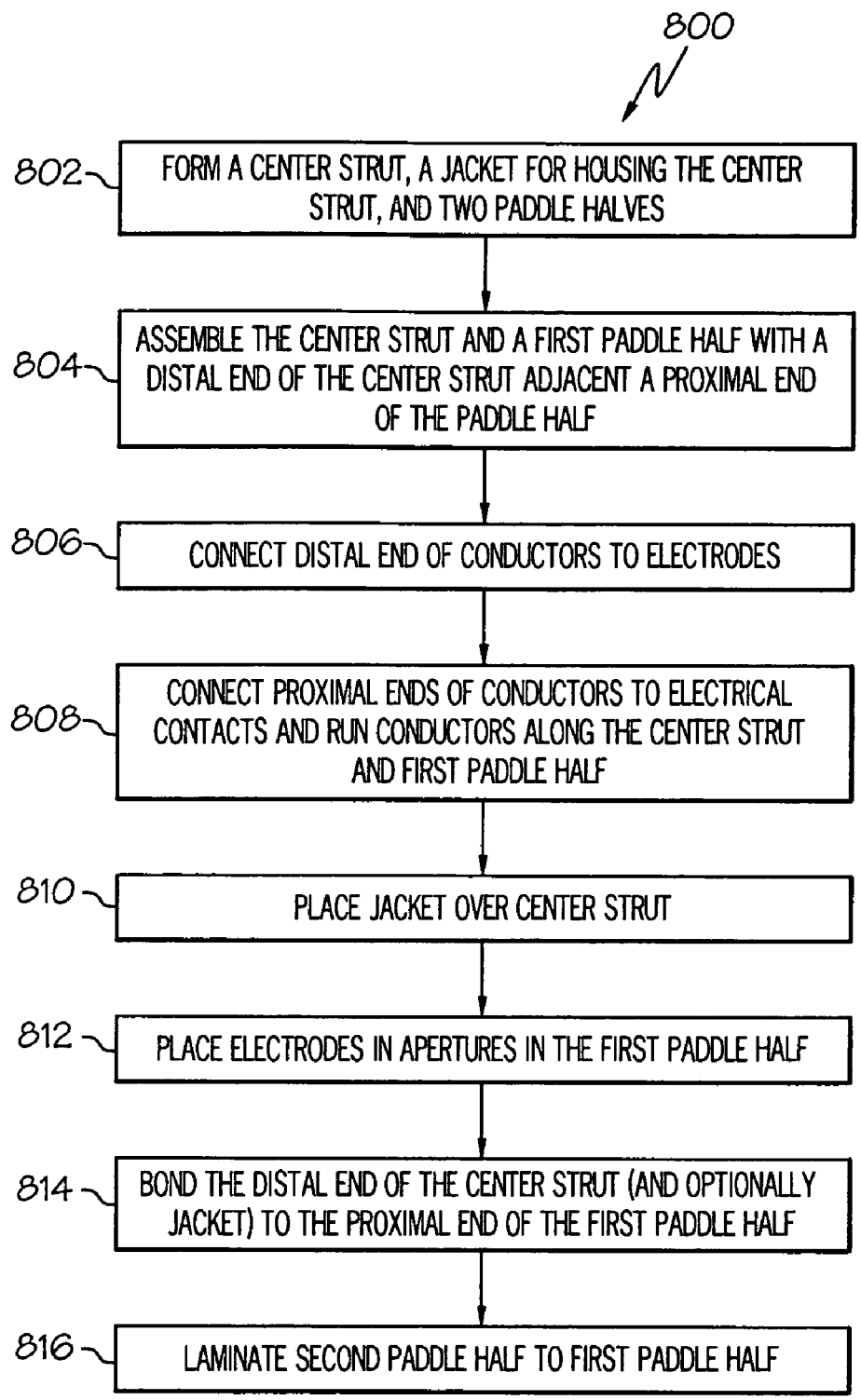

FIGS. 48 and 49 illustrate fourth and fifth exemplary embodiments of a method of manufacturing a medical lead. In FIG. 48, the exemplary method 700 comprises (a) forming a center strut, a jacket for housing the center strut, and two paddle halves (step 702 in FIG. 48); (b) assembling the center strut and a first paddle half with a distal end of the center strut adjacent a proximal end of the paddle half (step 704 in FIG. 48); (c) connecting distal end of conductors to electrodes (step 706); (d) placing electrodes in apertures in the first paddle half and run conductors along the first paddle half and center strut (step 708); (e) placing jacket over center strut (step 710); (f) connecting proximal ends of conductors to electrical contacts (step 712); (g) bonding the distal end of the center strut (and optionally jacket) to the proximal end of the first paddle half (step 714); and (h) laminating second paddle half to first paddle half (step 716).

In FIG. 49, the exemplary embodiment of the manufacturing method 800 comprises (a) forming a center strut, a jacket for housing the center strut, and two paddle halves (step 802); (b) assembling the center strut and a first paddle half with a distal end of the center strut adjacent a proximal end of the paddle half (step 804); (c) connecting distal end of conductors to electrodes (step 806); (d) connecting proximal ends of conductors to electrical contacts and run conductors along the center strut and first paddle half (step 808); (e) placing jacket over center strut (step 810); (f) placing electrodes in apertures in the first paddle half (step 812); (g) bonding the distal end of the center strut (and optionally jacket) to the proximal end of the first paddle half (step 814); and (h) laminating second paddle half to first paddle half (step 816).

Thus, exemplary embodiments of the paddle-style medical lead and method are disclosed. One skilled in the art will appreciate that the present invention can be practiced with embodiments other than those disclosed. The disclosed embodiments are presented for purposes of illustration and not limitation, and the present invention is limited only by the claims that follow.

The invention claimed is:

1. A method of manufacturing a medical lead comprising a lead body with at least one conductor and an elongate paddle having an electrode array, the method comprising:

forming at least first, second, third and fourth substantially flat and elongate members, each member having first and second ends;

butt bonding the first end of the first member to the second end of the second member to form a first section with the junction of the first end of the first member and the second end of the second member constituting a first butt bond, the first section having first and second major surfaces;

butt bonding the first end of the third member to the second end of the fourth member to form a second section with the junction of the first end of the third member and the second end of the fourth member constituting a second butt bond, the second section having first and second major surfaces;

placing at least one electrode in the first section exposed through the first major surface of the first member, and placing at least one conductor in electrical communication with the electrode along the second major surface of the first member;

attaching the first major surface of the second section to the second major surface of the first section to form the elongate paddle of the medical lead with the first butt bond longitudinally offset from the second butt bond.

2. The method of claim 1 wherein the step of attaching the first major surface of the second section to the second major surface of the first section including adhesively bonding the first major surface of the second section to the second major surface of the first section.

3. The method of claim 2 wherein the first, second, third and fourth substantially flat and elongate members including material selected from the group consisting of urethane and polyurethane, the step of adhesively bonding the first major surface of the second section to the second major surface of the first section including adhesively bonding with urethane adhesive.

4. The method of claim 1 wherein the step of forming at least first, second, third and fourth substantially flat and elongate members includes molding the first, second, third and fourth substantially flat and elongate members.

5. The method of claim 4 wherein:

the step of molding the first, second, third and fourth substantially flat and elongate members includes molding into the first and second members a path for receipt of at least one conductor, the path being arranged along the first and second sections, such that when the first and second members are butt bonded to form the first section, the path is arranged along the second major surface of the first section; and the step of placing at least one conductor in electrical communication with the electrode along the second major surface of the first member includes placing the conductor in the path.

6. The method of claim. 5 wherein the step of molding the first, second, third and fourth substantially flat and elongate members includes molding into each member a half channel arranged along each such that when the first and section sections are attached to form a paddle the half channels form a stylet lumen.

7. The method of claim 6 wherein the step of molding the first, second, third and fourth substantially flat and elongate members includes molding at least one aperture into at least one of the first and second members, the step of placing at least one electrode in the first section exposed through the first major surface of the first member includes placing the electrode in the aperture.

8. The method of claim 7 wherein the paddle define a longitudinal center line, and the at least one electrode has at least one lateral edge laterally offset from the center line, the method further comprising connecting the conductor to the lateral edge of the electrode such that tension along the conductor would tend to torque the electrode to relieve such tension.

9. The method of claim 8 wherein the step of connecting the conductor to the lateral edge of the electrode includes forming a connector, crimping the connector to the conductor and welding the connector to the lateral edge of the electrode.

10. The method of claim 1 wherein the step of forming at least first, second, third and fourth substantially flat and elongate members includes extruding the first, second, third and fourth substantially flat and elongate members.

11. A method of manufacturing a medical lead comprising a lead body with at least one conductor and an elongate paddle having an electrode array, the method comprising:
    forming a first section having a first butt bond by butt bonding an end of a first substantially flat and elongate member to an end of a second substantially flat and elongate member, the first section having a first and a second major surface;
    forming a second section having a second butt bond by butt bonding an end of a third substantially flat and elongate member to an end of a fourth substantially flat and elongate member, the second section having a first and a second major surface; and
    laminating the first section to the second section to form the elongate paddle of the medical lead with the first butt bond longitudinally offset from the second butt bond.

12. The method of claim 11 wherein the step of laminating the first section to the second section includes adhesively bonding the first major surface of the second section to the second major surface of the first section.

13. The method of claim 12 wherein the first, second, third and fourth substantially flat and elongate members include material selected from the group consisting of urethane and polyurethane, the step of adhesively bonding the first major surface of the second section to the second major surface of the first section including adhesively bonding with urethane adhesive.

14. The method of claim 11 wherein the step of forming at least first, second, third and fourth substantially flat and elongate members includes molding the first, second, third and fourth substantially flat and elongate members.

15. A medical lead for electrical stimulation or sensing, the medical lead comprising a generally flat paddle on the distal end of the lead body, the paddle having an electrode array comprising at least one electrode in electrical communication with the electrical conductor, the paddle being formed by a method comprising:
    forming a first section having a first butt bond by butt bonding an end of a first substantially flat and elongate member to an end of a second substantially flat and elongate member, the first section having a first and a second major surface;
    forming a second section having a second butt bond by butt bonding an end of a third substantially flat and elongate member to an end of a fourth substantially flat and elongate member, the second section having a first and a second major surface; and
    laminating the first section to the second section to form the elongate paddle of the medical lead with the first butt bond longitudinally offset from the second butt bond.

16. The medical lead of claim 15 wherein the first section is laminated to the second section by adhesively bonding the first major surface of the second section to the second major surface of the first section.

17. The medical lead of claim 16 wherein the first, second, third and fourth substantially flat and elongate members include material selected from the group consisting of urethane and polyurethane, the first major surface of the second section is adhesively bonded to the second major surface of the first section with urethane adhesive.

18. A method of manufacturing a medical lead comprising a lead body with at least one conductor and an elongate paddle having an electrode array, the method comprising:
    forming at least first, second, third and fourth substantially flat and elongate members, each member having first and second ends;
    butt bonding the first end of the first member to the second end of the second member to form a first section with the junction of the first end of the first member and the second end of the second member constituting a first butt bond, the first section having first and second major surfaces;
    placing at least one electrode in the first section exposed through the first major surface of the first member, and placing at least one conductor in electrical communication with the electrode along the second major surface of the first member;
    attaching the third member to a first portion of the second major surface of the first section with the first end of the third member longitudinally offset from the first butt bond and leaving a second portion of the second major surface of the first section exposed;
    attaching the fourth member to the second portion of the second major surface of the first section and butt bonding the second end of the fourth member to the first end of the third member with the butt bond of the first end of the third member and the second end of the fourth member constituting a second butt bond, and thus forming the elongate paddle of the medical lead with the first butt bond longitudinally offset from the second butt bond.

19. The method of claim 18 wherein the steps of attaching the third member to a first portion of the second major surface of the first section and attaching the fourth member to the second portion of the second major surface of the first section include:
    adhesively bonding the third member and the fourth member to the second major surface of the first section.

20. The method of claim 19 wherein the first, second, third and fourth substantially flat and elongate members including material selected from the group consisting of urethane and polyurethane, the steps of adhesively bonding the third member and the fourth member to the second major surface of the first section including adhesively bonding with urethane adhesive.

21. The method of claim 18 wherein the step of forming at least first, second, third and fourth substantially flat and elongate members includes molding the first, second, third and fourth substantially flat and elongate members.

22. The method of claim 21 wherein:
    the step of molding the first, second, third and fourth substantially flat and elongate members includes molding into the first and second members a path for receipt of at least one conductor, the path being arranged along the first and second sections, such that when the first and second members are butt bonded to form the first section, the path is arranged along the second major surface of the first section; and
    the step of placing at least one conductor in electrical communication with the electrode along the second major surface of the first member includes placing the conductor in the path.

23. The method of claim 22 wherein the step of molding the first, second, third and fourth substantially flat and elongate members includes molding into each member a half channel arranged along each such that the half channels form a stylet lumen when the paddle is formed.

24. The method of claim 23 wherein the step of molding the first, second, third and fourth substantially flat and elongate members includes molding at least one aperture into at least one of the first and second members, the step of placing at least one electrode in the first section exposed through the first major surface of the first member includes placing the electrode in the aperture.

25. The method of claim 24 wherein the paddle define a longitudinal center line, and the at least one electrode has at least one lateral edge laterally offset from the center line, the method further comprising connecting the conductor to the lateral edge of the electrode such that tension along the conductor would tend to torque the electrode to relieve such tension.

26. The method of claim 25 wherein the step of connecting the conductor to the lateral edge of the electrode includes forming a connector, crimping the connector to the conductor and welding the connector to the lateral edge of the electrode.

27. The method of claim 18 wherein the step of forming at least first, second, third and fourth substantially flat and elongate members includes extruding the first, second, third and fourth substantially flat and elongate members.

* * * * *